United States Patent
Farn et al.

(10) Patent No.: US 7,018,639 B1
(45) Date of Patent: Mar. 28, 2006

(54) VACCINE ANTIGENS OF *MORAXELLA*

(75) Inventors: Jacinta Farn, Essendon (AU); Richard Strugnell, Hawthorn (AU); Jan Tennent, Hawthorn East (AU)

(73) Assignees: Commonwealth Scientific and Industrial Research Organisation, Campbell (AU); The University of Melbourne, Parkville (AU)

( * ) Notice: Subject to any disclaimer, the term of this patent is extended or adjusted under 35 U.S.C. 154(b) by 0 days.

(21) Appl. No.: 10/069,799

(22) PCT Filed: Aug. 31, 2000

(86) PCT No.: PCT/AU00/01048

§ 371 (c)(1),
(2), (4) Date: Jul. 19, 2002

(87) PCT Pub. No.: WO01/16172

PCT Pub. Date: Mar. 8, 2001

(30) Foreign Application Priority Data

Aug. 31, 1999 (AU) .................................... PQ2571

(51) Int. Cl.
*A61K 39/02* (2006.01)
*C12P 21/04* (2006.01)
*C07H 21/02* (2006.01)
*C07H 21/04* (2006.01)

(52) U.S. Cl. ................ 424/251.1; 424/234; 424/200.1; 424/190.1; 435/69.7; 536/23.1; 536/23.4; 536/24.3

(58) Field of Classification Search ............. 424/184.1, 424/185.1, 190.1, 192.1, 200.1, 234.1, 251.1; 435/69.1, 69.7; 536/23.4, 23.1, 24.3
See application file for complete search history.

(56) References Cited

U.S. PATENT DOCUMENTS 6,096,320 A * 8/2000 Potter et al. ............. 424/255.1

FOREIGN PATENT DOCUMENTS

EP 0 146 523 A2 6/1985
WO 90/07525 7/1990

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67.*
Billson, F. M. et al. (1994) "A haemolytic cell-free preparation of *Moraxella bovis* confers protection against Infectious Bovine Keratoconjunctivitis" *FEMS Microbiology Letters* 124:69-73.
Bourgeau, G. et al. (1992) *Infection and Immunity* 60(8): 3186-3192.
Frank, S. K. et al. (Feb. 1981) "Hydrolytic Enzymes of *Moraxella bovis*" *Journal of Clinical Microbiology* 13(2): 269-271.
Hoien-Dalen, P.S. et al. (Feb. 1990) "Comparative characterization of the leukocidic and hemolytic activity of *Moraxella bovis*" *American Journal of Veterinary Research* 51(2):191-196.
Pugh, G.W. et al. (1977) *Am. J. Vet. Res.* 38:1519-1522.
Upton C. et al. (1995) *Trends Biochem Sci.* 20(5):178-179.

* cited by examiner

*Primary Examiner*—Lynette R. F. Smith
*Assistant Examiner*—Padma Baskar
(74) *Attorney, Agent, or Firm*—Greenlee Winner and Sullivan, PC

(57) ABSTRACT

The present invention relates to antigens of *Moraxella*, in particular, *Moraxella bovis*, nucleic acid sequences encoding these antigens and formulations for use in raising an immune response against *Moraxella*.

3 Claims, 7 Drawing Sheets

```
1    ttctcatgtt tgacagctta tcatcgataa gctttaatgc ggtagtttat cacagttaaa ttgctaacgc agtcaggcac cgtgtatgaa
91   atctaacaat gcgctcatcg tcatcctcgg caccgtcacc ctggatgctg taggcatagg cttggttatg ccggtactgc cgggcctctt
181  gcgggatatc gtccattccg acagcatcgc cagtcactat ggcgtgctgc tagcgctata tgcgttgatg caattctat gcgcacccgt
271  tctcggagca ctgtccgacc gctttggccg ccgcccagtc ctgctcgctt cgctacttgg agccactatc gactacgcga tcatgcgcac
361  cacacccgtc ctgtggatca ataattaatg aacatatata ctctatttaa tatttcttat ttattcgtaa tattgccata aaaataatac
451  attactcta tattaactaa actgttaata tttgtaaata ataaacattt gtttatctaa aaaatataat aatataaatc aagcaattac
541  aatcttattct ttgaaaatac aataatactg caattgctta atctagacat taagtttatt tttgattaaa attgccaaaa cctgtgtaaa
631  taagtttcac cgaattgata ctttaagggt atcaatattg caacatggta aatgaTTGCT atgttgttgg gcattgcaTA AATCgtctat
721  aataacttgt tatggatgat tgatggcaat gataaactta gtgacaatga taaacgcaaA GAGAtgtaat atgtcattac aaactcaacc
1                                                                                    M  S  L  Q  T  Q
811  tgccaagaga gggttctatg ttaagccttt aagtatggct tgcatgctgg taactagtgc tagtagtacg gtaagttatg ccaactcagc
7    P  A  K  R  G  F  Y  V  K  P  L  S  M  A  C  M  L  V  I  S  A  S  S  T  V  S  Y  A  N  S
901  tccaatgatt gttgattcac agtacaatag ttctaaatac tctttctacg attactattt agatttcctt aaacgtttta gaccaactcc
37   A  P  M  I  V  D  S  Q  Y  N  S  S  K  Y  S  F  Y  D  Y  Y  L  D  F  L  K  R  F  R  P  T
991  aactccagtg ccaagccctg tgagaccggc tcctgaactc gttcgtccga ccccagcccc gattccggct ccaacgcctg tgccaacacc
67   P  T  P  V  P  S  P  V  R  P  A  P  E  L  V  R  P  T  P  A  P  I  P  A  P  T  P  V  P  T
1081 ggcaccaatt agtggcggta tatcaggtag ctatattgct ccagtatcgc catcagaggt gagacagcct gattacacaa gaccgcgttca
97   P  A  P  I  S  G  G  I  S  G  S  Y  I  A  P  V  S  P  S  E  V  R  Q  P  D  Y  T  R  R  V
1171 agccaatcta aaacgcaacc aacctgcacc aagtgctggc acacgtacag gttatagtgt catggatacg tcaaataatt ctaatttgac
127  Q  A  N  L  K  R  N  Q  P  A  P  S  A  G  T  R  T  G  Y  S  V  M  D  T  S  N  N  S  N  L
1261 atctaaattt tatggcacaa ccgaagatgg ttatgccgag cgtcttgaca acctaaagaa caccattgat acacgtcaag ccaagtagg
157  T  S  K  F  Y  G  T  T  E  D  G  Y  A  E  R  L  D  N  L  K  N  T  I  D  T  R  Q  A  K  V
1351 tgtgattgat acaggcatta accgcttcaa ccgagacttg gttggtgcaa atgtgcatga tacacagatt gagtgtgttt ctgctggacg
187  G  V  I  D  T  G  I  N  R  F  N  R  D  L  V  G  A  N  V  H  D  T  Q  I  E  C  V  S  A  G
1441 ttccacctgc tatacgccaa aaatgattc aggcattgtt gaaatcccaa caacctctgc tagtggtagt catggcaacc aaatggcggc
217  R  S  T  C  Y  T  P  E  N  D  S  G  I  V  E  I  P  T  T  S  A  S  G  S  H  G  N  Q  M  A
1531 tgtcatcgct ggtaacaacg gcatgaccaa cgccaaaatc tacggcagtg acagtattga tcgacgttca aatggtggca accattctt
247  A  V  I  A  G  N  N  G  M  T  N  A  K  I  Y  G  S  D  S  I  D  R  R  S  N  G  G  N  H  F
1621 gatgatgcgt aagctgaacc aagaccatgg tgtcaagatt tttaacaact ctggggttc taacaacact gaccaatggt actacgatgc
277  L  M  M  R  K  L  N  Q  D  H  G  V  K  I  F  N  N  S  W  G  S  N  N  T  D  Q  W  Y  Y  D
1711 tcagcgccta aattacaatc ctactacagg acagattaat ccaaatcctt acagaaccag tattaccaat gctgaagtga ctttgcctgt
307  A  Q  R  L  N  Y  N  P  T  T  G  Q  I  N  P  N  P  Y  R  T  S  I  T  N  A  E  V  T  L  P
1801 cattcatgat cttattatga atcgtgactc gcttatcatt aaagcaacag gtaacgaagg cttgaacgat gctcatgatg aaaacctagc
337  V  I  H  D  L  I  M  N  R  D  S  L  I  I  K  A  T  G  N  E  G  L  N  D  A  H  D  E  N  L
1891 accgctcatg aacagcaact tcaaaaaagg tttcattact gtctcctcgc ctagaagaa tttggtaaa gcgaatcatt gtggtcgaac
367  A  P  L  M  N  S  N  F  K  K  G  F  I  T  V  S  S  P  R  E  D  F  G  K  A  N  H  C  G  R
1981 tgccgaatgg tgtgtatccg caacatcatc tacccaaaat tacgccaacg atggcagact gagtagctat aagggtacat cacctgcaac
397  T  A  E  W  C  V  S  A  T  S  S  T  Q  N  Y  A  N  D  G  R  L  S  S  Y  K  G  T  S  P  A
2071 cgctcgtgtg tccggcacgg cagtgctcgt gcaatctgct tatcctcgga tgaaaaatga aaatatctct caaaccattt tgggtactgc
427  T  A  R  V  S  G  T  A  V  L  V  Q  S  A  Y  P  H  M  K  N  E  N  I  S  Q  T  I  L  G  T
2161 caaggatttc tcagagatta ctgccaattc acctaatggc taccaaggac taagaaaggt tagtagattg ccatctggtt attacggctc
457  A  K  D  F  S  E  I  T  A  N  S  P  N  G  Y  Q  G  L  R  K  V  S  R  L  P  S  G  Y  Y  G
2251 ttattacact gacaatcagg gtaattteta tgttcctggc aatgtcaatt gggaaaaccg tcgaattgtc gctaatcata acggcaagaa
487  S  Y  Y  T  D  N  Q  G  N  F  Y  V  P  G  N  V  N  W  E  N  R  R  I  V  A  N  H  N  G  K
2341 cattacatgg gaagatggtt ggggttgtt agatccagaa gcggccgcta aaggttatgg tggttctat tgggataatg tggaattaga
517  N  I  T  W  E  D  G  W  G  L  L  D  P  E  A  A  A  K  G  Y  G  G  F  Y  W  D  N  V  E  L
2431 cactaaaggc acgcctttat ctgtattcta caatgaccta aaaggtgata aaggcttac caaaaaaggt gaagtaaac ttgtctttac
547  D  T  K  G  T  P  L  S  V  F  Y  N  D  L  K  G  D  K  G  F  T  K  K  G  E  G  K  L  V  F
2521 tggtaataat agctataaag gcgactctgt catcgagggt ggtcactag aagtaaatgg taacaacggt ggttcaacca tggttgttaa
577  T  G  N  N  S  Y  K  G  D  S  V  I  E  G  G  S  L  E  V  N  G  N  N  G  S  T  M  V  V
2611 aggtggtgaa ctaacagggtt atggtaatgt agctaatgtt cgtcaaacag gtggttgggt taacaacgaa ggtaacctaa acatcagagg
607  K  G  G  E  L  T  G  Y  G  N  V  A  N  V  R  Q  T  G  G  W  V  N  N  E  G  N  L  N  I  R
```

```
   1 tgggcagata acccatcaaa gacccaaagc aacccataaa tcaaaaaaac actrgtaatt tgtgtaatat cttgttacac tttacaagtg 91 tttttacttt gaaagcaact cagagagtaa taatgaaaaa atccgccttt gccaaatact cagcacttgc cctaatggtt gggatgtgcc
   1                                               M  K  K  S  A  F  A  K  Y  S  A  L  A  L  M  V  G  M  C 181 tgcacaccgc ttacgccaag gagtttagcc aagtcatcat tttttgggac agcttgtccg atacaggtcg cctaaaagat atggtcgccc
  20  L  H  T  A  Y  A  K  E  F  S  Q  V  I  I  F  G  D  S  L  S  D  T  G  R  L  K  D  M  V  A 271 gaaaagatgg cacccttggc aacaccttac agccatcttt taccaccaac cccgaccctg tatggtcaag cttatttgcc caaagttatg
  50  R  K  D  G  T  L  G  N  T  L  Q  P  S  F  T  T  N  P  D  P  V  W  S  S  L  F  A  Q  S  Y 361 gcaaaaccgc cagtgccaac acgccctaca atcccactgg cactaactat gccgtgggcg gagctcgctc tggctcggag gtcaattgga
  80  G  K  T  A  S  A  N  T  P  Y  N  P  T  G  T  N  Y  A  V  G  G  A  R  S  G  S  E  V  N  W 451 atggttttgt gaatgtaccc tccaccaaaa cgcaaatcac cgaccatttg accgccacag gtggcaaagc cgaccctaat accctgtatg
 110  N  G  F  V  N  V  P  S  T  K  T  Q  I  T  D  H  L  T  A  T  G  G  K  A  D  P  N  T  L  Y 541 ccatttggat tggctctaat gacttaattt cagcttctca agccaccaca acagccgaag cccaaaacgc cattaaaggt gcggtaactc
 140  A  I  W  I  G  S  N  D  L  I  S  A  S  Q  A  T  T  T  A  E  A  Q  N  A  I  K  G  A  V  T 631 gcaccgtgat agacatcgaa acactcaatc aagcagggc gacaaccatt ttggtgccaa atgtgcctga tttgagcctc acgcccgag
 170  R  T  V  I  D  I  E  T  L  N  Q  A  G  A  T  T  I  L  V  P  N  V  P  D  L  S  L  T  P  R 721 ccatctatgg cgaaagcctc atggcaggcg tgcaagacaa agccaaactc gcctcaagtc tgtataatag cggtctgttt gaagcattaa
 200  A  I  Y  G  E  S  L  M  A  G  V  Q  D  K  A  K  L  A  S  S  L  Y  N  S  G  L  F  E  A  L 811 atcaatccac cgccaacatc atccctgcca acacctttgc cctactccaa gaagcgacca caataaaga agcctttggt tttaaaaaca
 230  N  Q  S  T  A  N  I  I  P  A  N  T  F  A  L  L  Q  E  A  T  T  N  K  E  A  F  G  F  K  N 901 cgcaaggcgt ggcgtgtcaa atgcccgctc gtaccacagg ggcggatgat gtggcttcta cttccttggc atgtaccaaa gccaatctta
 260  T  Q  G  V  A  C  Q  M  P  A  R  T  T  G  A  D  D  V  A  S  T  S  L  A  C  T  K  A  N  L 991 tagaaaacgg ggcaaatgac acctacgcct ttgccgatga cattcaccca tcgggacgca cgcaccgcat tttggcacag tattaccgtt
 290  I  E  N  G  A  N  D  T  Y  A  F  A  D  D  I  H  P  S  G  R  T  H  R  I  L  A  Q  Y  Y  R 1081 ctatcatgga cgcccctact cacatgggta aactctcagg cgagcttgtc aaaacaggtt cagcccacga ccgtcatgtt taccgtcagc
 320  S  I  M  D  A  P  T  H  M  G  K  L  S  G  E  L  V  K  T  G  S  A  H  D  R  H  V  Y  R  Q 1171 ttgacaggcc tagtggctca cagcacagca tttgggcaaa cgtccatgcc agcgaccgta ccgaccccac cacccaaatc ggcttggacg
 350  L  D  R  L  S  G  S  Q  H  S  I  W  A  N  V  H  A  S  D  R  T  D  P  T  T  Q  I  G  L  D 1261 tggcaggttc atcaagccat acaggggcgt atctgagcca ccaaaaccaa gattatgtgc tggatgacac cctatcatca gatgtcaaaa
 380  V  A  G  S  S  S  H  T  G  A  Y  L  S  H  Q  N  Q  D  Y  V  L  D  D  T  L  S  S  D  V  K 1351 ccattggcat ggggctgtat catcgccatg acatcggcaa tgtccgtcta aaaggcgtgg caggtatcga ccgacttagc gtggatacgc
 410  T  I  G  M  G  L  Y  H  R  H  D  I  G  N  V  R  L  K  G  V  A  G  I  D  R  L  S  V  D  T 1441 accgccatat cgactggagg ggggcaagcc gttcgcacac ggcagacacc accgccagac gttttcatgc agggctacaa gccgctatg
 440  H  R  H  I  D  W  E  G  A  S  R  S  H  T  A  D  T  T  A  R  R  F  H  A  G  L  Q  A  S  Y 1531 gcatagacat gggcaaagcc accgtgccgt cgcttatcgg cgtacatgcc caaaaagtca aagtgcgtga tttggtagag aatgagccta
 470  G  I  D  M  G  K  A  T  V  R  P  L  I  G  V  H  A  Q  K  V  K  V  R  D  L  V  E  N  E  P 1621 ccctatccac cgccatgcgt tttggcgagc aagaacaaaa gtccctacaa ggcgagattg gcgtcgatgt ggcttatccg attagccctg
 500  T  L  S  T  A  M  R  F  G  E  Q  E  Q  K  S  L  Q  G  E  I  G  V  D  V  A  Y  P  I  S  P 1711 ctttgactct gacgggcggt atcgctcacg ctcatgagtt taacgatgat gaacgcacca ttaatgccac tttaacctcc attcgtgaat
 530  A  L  T  L  T  G  G  I  A  H  A  H  E  F  N  D  D  E  R  T  I  N  A  T  L  T  S  I  R  E 1801 acacgaaggg ctttaataca agcgttagca ccgacaaatc tcacgccacc accgctcatc tgggcgtaca agggcaactt ggcaaggcaa
 560  Y  T  K  G  F  N  T  S  V  S  T  D  K  S  H  A  T  A  H  L  G  V  Q  G  Q  L  G  K  A 1891 atattcatgc aggcgttcac gccacccacc aagacagcga tacagacgtg ggtggttcgc ttggggttcg cttgatgttt tgattggctt
 590  N  I  H  A  G  V  H  A  T  H  Q  D  S  D  T  D  V  G  G  S  L  G  V  R  L  M  F  -

1981 ttaaagataa aaagtggtat catgccactt tttatttttgc caaaaatcta tgtttgagta catcaaagcc tttcacatca tcgccatgcg 2071 atgataagct gtcaaacatg ag
```

Figure 2

(i) Dalton 2d / *M. bovis*
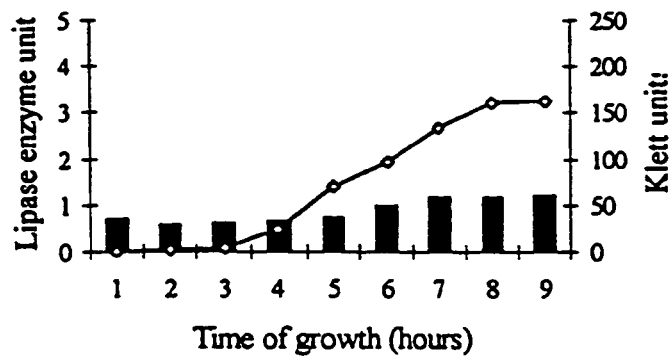
(ii) pMB1 / MC1061
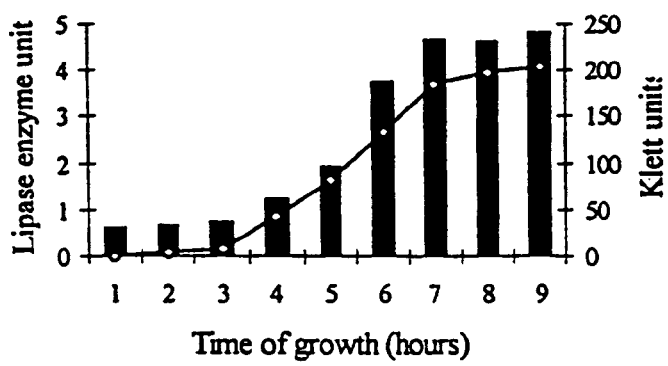
Figure

```
  1  atgagaacgt tattttcaga tgaattgttt agagcgattc gtgtagatgg aaattcatcg catggtaaga tatctgaatt ttatggaaag
     M  R  T  L  F  S  D  E  L  F  R  A  I  R  V  D  G  N  S  S  H  G  K  I  S  E  F  Y  G  K 91  tctgttgatt caaaattagc ctcaagaata tttgcacaat atcacgaaga tttgacgagc aaattgtcaa ctcagaataa tttattata
     S  V  D  S  K  L  A  S  R  I  F  A  Q  Y  H  E  D  L  T  S  K  L  S  T  Q  N  N  F  I  I 181  tctaaagata attaatacaa ccttttctaa cacaacgagg agagacatat tatgtccaat ataaatgtaa ttaaatctaa tattcaagca
  1  S  K  D  N  -                                         M  S  N  I  N  V  I  K  S  N  I  Q  A 271  ggcttgaatt caacaaagtc tggattaaaa aatctttact tggctattcc caaagattat gatccgcaaa aaggtgggac tttaaatgat
 14  G  L  N  S  T  K  S  G  L  K  N  L  Y  L  A  I  P  K  D  Y  D  P  Q  K  G  G  T  L  N  D 361  tttattaaag ctgctgatga attaggtatt gctcgtttag cagaagagcc taatcacact gaaacagcaa aaaaatctgt tgacacagta
 44  F  I  K  A  A  D  E  L  G  I  A  R  L  A  E  E  P  N  H  T  E  T  A  K  K  S  V  D  T  V 451  aatcagtttc tctctctcac acaaactggt attgctattt ctgcaacaaa attagaaaag ttcttacaaa aacattctac caataagtta
 74  N  Q  F  L  S  L  T  Q  T  G  I  A  I  S  A  T  K  L  E  K  F  L  Q  K  H  S  T  N  K  L 541  gccaaagggt tagacagtgt agaaaatatt gatcgtaaat taggtaaagc aagtaatgta ttatcaacat taagctcttt tttgggcact
104  A  K  G  L  D  S  V  E  N  I  D  R  K  L  G  K  A  S  N  V  L  S  T  L  S  S  F  L  G  T 631  gcattagcgg gtatagaact tgattcttta atcaaaaaag gtgatgctgc acctgatgct ttggctaaag ctagtattga cttgattaat
134  A  L  A  G  I  E  L  D  S  L  I  K  K  G  D  A  A  P  D  A  L  A  K  A  S  I  D  L  I  N 721  gagataattg gtaatctatc tcagagtact caaacgattg aagcattttc ttcacagtta gcaaagttag gttctactat atcgcaggct
164  E  I  I  G  N  L  S  Q  S  T  Q  T  I  E  A  F  S  S  Q  L  A  K  L  G  S  T  I  S  Q  A 811  aaaggcttct ctaatatagg aaacaagttg caaaacttaa attttctaa aacaaatctt ggtttggaaa taattactgg tttgctatca
194  K  G  F  S  N  I  G  N  K  L  Q  N  L  N  F  S  K  T  N  L  G  L  E  I  I  T  G  L  L  S 901  ggcattctg caggctttgc tttagcggat aaaaatgcat cgactggcaa aaaagttgct gcaggctttg aattaagcaa tcaagttatt
224  G  I  S  A  G  F  A  L  A  D  K  N  A  S  T  G  K  K  V  A  A  G  F  E  L  S  N  Q  V  I 991  ggtaatgtaa caaaagcaat ttcttcatat gttttagcac aacgtgttgc tgctggtcta tcaactactg gtgctgttgc tgctttaatt
254  G  N  V  T  K  A  I  S  S  Y  V  L  A  Q  R  V  A  A  G  L  S  T  T  G  A  V  A  A  L  I 1081 acttcatcga ttatgttggc aattagtcct ttggcattta tgaatgcagc agataaattc aatcatgcta atgctcttga tgagtttgca
284  T  S  S  I  M  L  A  I  S  P  L  A  F  M  N  A  A  D  K  F  N  H  A  N  A  L  D  E  F  A 1171 aaacaattcc gaaaatttgg ctatgatggg gatcattat tggctgaata tcagcgtggt gtgggtacta ttgaagcttc attaactaca
314  K  Q  F  R  K  F  G  Y  D  G  D  H  L  L  A  E  Y  Q  R  G  V  G  T  I  E  A  S  L  T  T 1261 attagtacgg cattaggtgc agtttctgct ggtgtttccg ctgctgctgt aggatctgct gttggtacac cgattgcact attagttgca
344  I  S  T  A  L  G  A  V  S  A  G  V  S  A  A  A  V  G  S  A  V  G  T  P  I  A  L  L  V  A 1351 ggtgttacag gattgatctc tggaactta gaagcgtcta aacaggcaat gtttgaaagt gttgctaacc gttacaagg taaatttta
374  G  V  T  G  L  I  S  G  I  L  E  A  S  K  Q  A  M  F  E  S  V  A  N  R  L  Q  G  K  I  L 1441 gagtgggaaa agcaaaatgg cggtcagaac tattttgata aaggctatga ttctcgttat gctgcttatt tagctaataa cttaaaattt
404  E  W  E  K  Q  N  G  G  Q  N  Y  F  D  K  G  Y  D  S  R  Y  A  A  Y  L  A  N  N  L  K  F 1531 ttgtctgagc taaataaaga gttggaagct gaacgtgtta ttgcaatcac ccaacaacgt tgggataata atattggtga gttagcaggt
434  L  S  E  L  N  K  E  L  E  A  E  R  V  I  A  I  T  Q  Q  R  W  D  N  N  I  G  E  L  A  G 1621 attaccaaat tgggtgaacg cattaagagc ggaaaagctt atgcagatgc ttttgaagat ggcaagaaag ttgaagctgg ttccaatatt
464  I  T  K  L  G  E  R  I  K  S  G  K  A  Y  A  D  A  F  E  D  G  K  K  V  E  A  G  S  N  I 1711 acttggatg ctaaaactgg tatcatagac attagtaatt caaatgggaa aaaaacgcaa gcgttgcatt tcacttcgcc tttgttaaca
494  T  L  D  A  K  T  G  I  I  D  I  S  N  S  N  G  K  K  T  Q  A  L  H  F  T  S  P  L  L  T 1801 gcaggaactg aatcacgtga acgtttaact aatggtaaat actcttatat taataagtta aaattcggac gtgtaaaaaa ctggcaagtt
524  A  G  T  E  S  R  E  R  L  T  N  G  K  Y  S  Y  I  N  K  L  K  F  G  R  V  K  N  W  Q  V 1891 acagatggag aggctagttc taaattagat ttctctaaag ttattcagcg tgtagccgag acagaaggca cagacgagat tggtctaata
554  T  D  G  E  A  S  S  K  L  D  F  S  K  V  I  Q  R  V  A  E  T  E  G  T  D  E  I  G  L  I 1981 gtaaatgcaa aagctggcaa tgacgatatc tttgttggtc aaggtaaaat gaatattgat ggtggagatg gacacgatcg tgtcttctat
584  V  N  A  K  A  G  N  D  D  I  F  V  G  Q  G  K  M  N  I  D  G  G  D  G  H  D  R  V  F  Y 2071 agtaaagacg gaggatttgg taatattact gtagatggta cgagtgcaac agaagcaggc agttatacag ttaatcgtaa ggttgctcga
614  S  K  D  G  G  F  G  N  I  T  V  D  G  T  S  A  T  E  A  G  S  Y  T  V  N  R  K  V  A  R 2161 ggtgatatct accatgaagt tgtgaagcgt caagaaacca aggtgggtaa acgtactgaa actatccagt atcgtgatta tgaattaaga
644  G  D  I  Y  H  E  V  V  K  R  Q  E  T  K  V  G  K  R  T  E  T  I  Q  Y  R  D  Y  E  L  R 2251 aaagttgggt atggttatca gtctaccgat aatttgaaat cagtagaaga agtaattggt tctcaattta tgatgtatt caaaggttct
674  K  V  G  Y  G  Y  Q  S  T  D  N  L  K  S  V  E  E  V  I  G  S  Q  F  N  D  V  F  K  G  S 2341 aaattcaacg acatattcca tagtggtgaa ggtgatgatt tactcgatgg tggtgctggt gacgaccgct tgtttggtgg taaaggcaac
704  K  F  N  D  I  F  H  S  G  E  G  D  D  L  L  D  G  G  A  G  D  D  R  L  F  G  G  K  G  N
```

Figure 5

```
2431 gatcgacttt ctggagatga aggcgatgat ttactcgatg gcggttctgg tgatgatgta ttaaatggtg gtgctggtaa tgatgtctat
 734    D  R  L   S  G  D   E  G  D  D   L  L  D   G  G  S   G  D  D  V   L  N  G   G  A  G  N  D  V  Y 2521 atctttcgga aaggtgatgg taatgatact ttgtacgatg gcacgggcaa tgataaatta gcatttgcag atgcaaatat atctgatatt
 764    I  F  R   K  G  D   G  N  D  T   L  Y  D   G  T  G   N  D  K  L   A  F  A   D  A  N   I  S  D  I 2611 atgattgaac gtaccaaaga gggtattata gttaaacgaa atgatcattc aggtagtatt aacataccaa gatggtacat aacatcaaat
 794    M  I  E   R  T  K   E  G  I  I   V  K  R   N  D  H   S  G  S  I   N  I  P   R  W  Y   I  T  S  N 2701 ttacaaaatt atcaaagtaa taaaacagat cataaaattg agcaactaat tggtaaagat ggtagttata tcacttccga tcaaattgat
 824    L  Q  N   Y  Q  S   N  K  T  D   H  K  I   E  Q  L   I  G  K  D   G  S  Y   I  T  S   D  Q  I  D 2791 aaaattttgc aagataagaa agatggtaca gtaattacat ctcaagaatt gaaaaagctt gctgatgaga ataagagcca aaaattatct
 854    K  I  L   Q  D  K   K  D  G  T   V  I  T   S  Q  E   L  K  K  L   A  D  E   N  K  S   Q  K  L  S 2881 gcttcggaca ttgcaagtag cttaaataag ctagttgggt caatggcact atttggtaca gcaaatagtg tgagttctaa cgccttacag
 884    A  S  D   I  A  S   S  L  N  K   L  V  G   S  M  A   L  F  G  T   A  N  S   V  S  S   N  A  L  Q 2971 ccaattacac aaccaactca aggaattttg gctccaagtg tttagtgatt taatttacta gacaatatca ccacccatat cattggttat
 914    P  I  T   Q  P  T   Q  G  I  L   A  P  S   V  -

3061 agattatgaa actagtgata tgggtggtga tacttcttta attagactta atttacaaac ccttaatagt aatttagtta tgatagatta
                           M  G  G   D  T  S  L   I  R  L   N  L  Q   T  L  N  S   N  L  V   M  I  D 3151 tgctcaacaa cctgctctat ctgctctggt tatccttgcc aaatactatg gtatttctgc aagtccagca gacattatgc atcgactggc
        Y  A  Q  Q   P  A  L   S  A  L   V  I  L  A   K  Y  Y   G  I  S   A  S  P   A  D  I  M   H  R  L 3241 aaaaaagttg
        A  K  K  L
```

Figure 5 (continued)

SEQUENCE LISTING

```
<160> NUMBER OF SEQ ID NOS: 9

<210> SEQ ID NO 1
<211> LENGTH: 1114
<212> TYPE: PRT
<213> ORGANISM: Moraxella bovis

<400> SEQUENCE: 1

Met Ser Leu Gln Thr Gln Pro Ala Lys Arg Gly Phe Tyr Val Lys Pro
  1               5                  10                  15

Leu Ser Met Ala Cys Met Leu Val Ile Ser Ala Ser Ser Thr Val Ser
             20                  25                  30

Tyr Ala Asn Ser Ala Pro Met Ile Val Asp Ser Gln Tyr Asn Ser Ser
         35                  40                  45

Lys Tyr Ser Phe Tyr Asp Tyr Tyr Leu Asp Phe Leu Lys Arg Phe Arg
     50                  55                  60

Pro Thr Pro Thr Pro Val Pro Ser Pro Val Arg Pro Ala Pro Glu Leu
 65                  70                  75                  80

Val Arg Pro Thr Pro Ala Pro Ile Pro Ala Pro Thr Pro Val Pro Thr
                 85                  90                  95

Pro Ala Pro Ile Ser Gly Gly Ile Ser Gly Ser Tyr Ile Ala Pro Val
            100                 105                 110

Ser Pro Ser Glu Val Arg Gln Pro Asp Tyr Thr Arg Arg Val Gln Ala
        115                 120                 125

Asn Leu Lys Arg Asn Gln Pro Ala Pro Ser Ala Gly Thr Arg Thr Gly
    130                 135                 140

Tyr Ser Val Met Asp Thr Ser Asn Asn Ser Asn Leu Thr Ser Lys Phe
145                 150                 155                 160

Tyr Gly Thr Thr Glu Asp Gly Tyr Ala Glu Arg Leu Asp Asn Leu Lys
                165                 170                 175

Asn Thr Ile Asp Thr Arg Gln Ala Lys Val Gly Val Ile Asp Thr Gly
            180                 185                 190
```

-continued

```
Ile Asn Arg Phe Asn Arg Asp Leu Val Gly Ala Asn Val His Asp Thr
        195                 200                 205

Gln Ile Glu Cys Val Ser Ala Gly Arg Ser Thr Cys Tyr Thr Pro Glu
        210                 215                 220

Asn Asp Ser Gly Ile Val Glu Ile Pro Thr Thr Ser Ala Ser Gly Ser
225                 230                 235                 240

His Gly Asn Gln Met Ala Ala Val Ile Ala Gly Asn Asn Gly Met Thr
                245                 250                 255

Asn Ala Lys Ile Tyr Gly Ser Asp Ser Ile Asp Arg Arg Ser Asn Gly
                260                 265                 270

Gly Asn His Phe Leu Met Met Arg Lys Leu Asn Gln Asp His Gly Val
        275                 280                 285

Lys Ile Phe Asn Asn Ser Trp Gly Ser Asn Asn Thr Asp Gln Trp Tyr
        290                 295                 300

Tyr Asp Ala Gln Arg Leu Asn Tyr Asn Pro Thr Thr Gly Gln Ile Asn
305                 310                 315                 320

Pro Asn Pro Tyr Arg Thr Ser Ile Thr Asn Ala Glu Val Thr Leu Pro
                325                 330                 335

Val Ile His Asp Leu Ile Met Asn Arg Asp Ser Leu Ile Ile Lys Ala
                340                 345                 350

Thr Gly Asn Glu Gly Leu Asn Asp Ala His Asp Glu Asn Leu Ala Pro
        355                 360                 365

Leu Met Asn Ser Asn Phe Lys Lys Gly Phe Ile Thr Val Ser Ser Pro
        370                 375                 380

Arg Glu Asp Phe Gly Lys Ala Asn His Cys Gly Arg Thr Ala Glu Trp
385                 390                 395                 400

Cys Val Ser Ala Thr Ser Ser Thr Gln Asn Tyr Ala Asn Asp Gly Arg
                405                 410                 415

Leu Ser Ser Tyr Lys Gly Thr Ser Pro Ala Thr Ala Arg Val Ser Gly
                420                 425                 430

Thr Ala Val Leu Val Gln Ser Ala Tyr Pro Trp Met Lys Asn Glu Asn
        435                 440                 445

Ile Ser Gln Thr Ile Leu Gly Thr Ala Lys Asp Phe Ser Glu Ile Thr
        450                 455                 460

Ala Asn Ser Pro Asn Gly Tyr Gln Gly Leu Arg Lys Val Ser Arg Leu
465                 470                 475                 480

Pro Ser Gly Tyr Tyr Gly Ser Tyr Tyr Thr Asp Asn Gln Gly Asn Phe
                485                 490                 495

Tyr Val Pro Gly Asn Val Asn Trp Glu Asn Arg Arg Ile Val Ala Asn
                500                 505                 510

His Asn Gly Lys Asn Ile Thr Trp Glu Asp Gly Trp Gly Leu Leu Asp
        515                 520                 525

Pro Glu Ala Ala Lys Gly Tyr Gly Phe Tyr Trp Asp Asn Val
        530                 535                 540

Glu Leu Asp Thr Lys Gly Thr Pro Leu Ser Val Phe Tyr Asn Asp Leu
545                 550                 555                 560

Lys Gly Asp Lys Gly Phe Thr Lys Lys Gly Glu Gly Lys Leu Val Phe
                565                 570                 575

Thr Gly Asn Asn Ser Tyr Lys Gly Asp Ser Val Ile Glu Gly Gly Ser
        580                 585                 590

Leu Glu Val Asn Gly Asn Asn Gly Gly Ser Thr Met Val Val Lys Gly
        595                 600                 605
```

-continued

```
Gly Glu Leu Thr Gly Tyr Gly Asn Val Ala Asn Val Arg Gln Thr Gly
    610             615                 620
Gly Trp Val Asn Asn Glu Gly Asn Leu Asn Ile Arg Gly Asp Tyr Asn
625             630                 635                 640
Ile Asn Thr Gln Arg Gly Val Asp Ala Gly Leu Lys Ala Gln Phe Gly
                645                 650                 655
Asn Met Leu Thr Val Asp Gly Lys Ala Lys Leu Gly Gly Thr Leu Asn
            660                 665                 670
Leu Thr Gly Glu Thr Lys Asp Gly Ile Ile Ser Lys Ser Gly Ser Arg
        675                 680                 685
Ser Thr Val Leu Arg Ala Lys Arg Gly Leu Glu Gly Gln Phe Asp Asn
    690                 695                 700
Tyr Arg Ser Ser Asn Pro Leu Phe Glu Val Thr Asn Val Glu Tyr Thr
705                 710                 715                 720
Pro Glu Val Asp Arg Asn Gly Arg Val Val Gly Ser Arg Thr Asn
                725                 730                 735
Asn Asp Val Gln Val Thr Ala Lys Arg Leu Ser Ala Gly Asn Val Val
            740                 745                 750
Tyr Gly Ile Ser Met Asn Asp Ser Gly Ser Arg Val Ala Gln Asn Leu
        755                 760                 765
Asp Lys Val Leu Asn Asp Leu Asp Lys Lys Gln Glu Thr Gln Gly Ser
    770                 775                 780
Leu Thr Ser Asp Glu Lys Gln Phe Ala Asn Arg Val Phe Thr Gly Phe
785                 790                 795                 800
Glu Asn Met Asn Ser Gly Ala Glu Ser Lys Leu Ser Thr Val Ser Thr
                805                 810                 815
Asn Arg Glu Leu Tyr Lys Leu Asp Pro Thr Phe Tyr Ala Asp Ser Ala
            820                 825                 830
Leu Asn Ala Val Glu Asp Ser Ala Asn His Ala Thr Glu Phe Gly Lys
        835                 840                 845
Arg Val Ser Ala Pro Arg Gly Val Trp Gly Asn Ile Ser His His Asp
    850                 855                 860
Tyr Asp Val Glu Leu Glu His Ala Thr Ser Ala Arg Lys Gly Asn Asn
865                 870                 875                 880
Ile Ser Val Gly Ala Ser Thr Gln Thr Ala Ala Asp Ile Ser Val Gly
                885                 890                 895
Ala Gln Leu Asp Val Ser Lys Leu Asp Leu Glu Glu Ser Val Tyr Gly
            900                 905                 910
Ile Gly Asn Lys Thr Lys Thr Asp Ser Ile Gly Leu Thr Val Gly Ala
        915                 920                 925
Ser Lys Lys Leu Gly Asp Ala Tyr Leu Ser Gly Trp Val Lys Gly Ala
    930                 935                 940
Lys Val Asp Thr Glu Ala Asn Arg Gly Glu Asn Ser Asn Lys Val Glu
945                 950                 955                 960
Tyr Asn Gly Lys Leu Tyr Gly Ala Gly Ile Gln Ala Gly Thr Asn Ile
                965                 970                 975
Asp Thr Ala Ser Gly Val Ser Val Gln Pro Tyr Ala Phe Val Asn His
            980                 985                 990
Gln Gln Tyr Lys Asn Asp Gly Ser Phe Asn Asp Gly Leu Asn Val Val
        995                 1000                1005
Asp Asp Ile Glu Ala Lys Gln Thr Gln Val Gly Val Gly Ala Asp Met
    1010                1015                1020
Val Phe Gln Ala Thr Pro Ala Leu Gln Leu Thr Gly Gly Val Gln Val
```

|  |  |  |  |  |
|---|---|---|---|---|
| 1025 | 1030 | 1035 | 1040 | |

Ala His Ala Val Ser Arg Asp Thr Asn Leu Asp Thr Arg Tyr Val Gly
                1045                      1050                      1055

Thr Ala Thr Asp Val Gln Tyr Gly Thr Trp Asp Thr Asp Lys Thr Lys
          1060                      1065                      1070

Trp Ser Ala Lys Val Gly Ala Asn Tyr Asn Val Thr Pro Asn Ser Gln
        1075                      1080                      1085

Val Gly Leu Asn Tyr Ser Tyr Thr Gly Ser Gly Asp Ser Asp Ala Ser
1090                      1095                      1100

Gln Val Gly Val Ser Phe Thr Ser Lys Phe
1105                    1110

<210> SEQ ID NO 2
<211> LENGTH: 4384
<212> TYPE: DNA
<213> ORGANISM: Moraxella bovis

<400> SEQUENCE: 2

| | | | | | |
|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccggtactgc | cgggcctctt | 180 |
| gcgggatatc | gtccattccg | acagcatcgc | cagtcactat | ggcgtgctgc | tagcgctata | 240 |
| tgcgttgatg | caatttctat | gcgcacccgt | tctcggagca | ctgtccgacc | gctttggccg | 300 |
| ccgcccagtc | ctgctcgctt | cgctacttgg | agccactatc | gactacgcga | tcatggcgac | 360 |
| cacacccgtc | ctgtggatca | ataattaatg | aacatatata | ctctatttaa | tatttcttat | 420 |
| ttattcgtaa | tattgccata | aaataataac | attatttcta | tattaactaa | actgttaata | 480 |
| tttgtaaata | ataaacattt | gtttatctaa | aaaataaat | aatataaatc | aagcaattac | 540 |
| aatcttattt | ttgaaaatac | aataatactg | caattgctta | atctagacat | taagtttatt | 600 |
| tttgattaaa | attgccaaaa | cttgtgtaaa | taagtttcac | cgaattgata | ctttaagggt | 660 |
| atcaatattg | caacatggta | aatgattgct | atgttgttgg | gcattgcata | aattgtctat | 720 |
| aataacttgt | tatggatgat | tgatggcaat | gataaactta | gtgacaatga | taaacgcaaa | 780 |
| gaggtgtaat | atgtcattac | aaactcaacc | tgccaagaga | gggttctatg | ttaagccttt | 840 |
| aagtatggct | tgcatgctgg | taattagtgc | tagtagtacg | gtaagttatg | ccaactcagc | 900 |
| tccaatgatt | gttgattcac | agtacaatag | ttctaaatac | tctttctacg | attactattt | 960 |
| agatttcctt | aaacgtttta | gaccaactcc | aactccagtg | ccaagccctg | tgagaccggc | 1020 |
| tcctgaactc | gttcgtccga | ccccagcccc | gattccggct | ccaacgcctg | tgccaacacc | 1080 |
| ggcaccaatt | agtggcggta | tatcaggtag | ctatattgct | ccagtatcgc | catcagaggt | 1140 |
| gagacagcct | gattacacaa | gacgcgttca | agccaatcta | aaacgcaacc | aacctgcacc | 1200 |
| aagtgctggc | acacgtacag | gttatagtgt | catggatacg | tcaaataatt | ctaatttgac | 1260 |
| atctaaattt | tatggcacaa | ccgaagatgg | ttatgccgag | cgtcttgaca | acctaaagaa | 1320 |
| caccattgat | acacgtcaag | ccaaagtagg | tgtgattgat | acaggcatta | accgcttcaa | 1380 |
| ccgagacttg | gttggtgcaa | atgtgcatga | tacacagatt | gagtgtgttt | ctgctggacg | 1440 |
| ttccacctgc | tatacgccag | aaaatgattc | aggcattgtt | gaaatcccaa | caacctctgc | 1500 |
| tagtggtagt | catggcaacc | aaatggcggc | tgtcatcgct | ggtaacaacg | gcatgaccaa | 1560 |
| cgccaaaatt | tacggcagtg | acagtattga | tcgacgttca | aatggtggca | accatttctt | 1620 |

```
gatgatgcgt aagctgaacc aagaccatgg tgtcaagatt tttaacaact cttggggttc    1680
taacaacact gaccaatggt actacgatgc tcagcgccta aattacaatc ctactacagg    1740
acagattaat ccaaatcctt acagaaccag tattaccaat gctgaagtga ctttgcctgt    1800
cattcatgat cttattatga atcgtgactc gcttatcatt aaagcaacag gtaacgaagg    1860
cttgaacgat gctcatgatg aaaacctagc accgctcatg aacagcaact tcaaaaaagg    1920
tttcattact gtctcctcgc ctagagaaga ttttggtaaa gcgaatcatt gtggtcgaac    1980
tgccgaatgg tgtgtatccg caacatcatc tacccaaaat tacgccaacg atggcagact    2040
gagtagctat aagggtacat cacctgcaac cgctcgtgtg tccggcacgg cagtgctcgt    2100
gcaatctgct tatccttgga tgaaaaatga aatatctct caaaccattt tgggtactgc     2160
caaggatttc tcagagatta ctgccaattc acctaatggc taccaaggac taagaaaggt    2220
tagtagattg ccatctggtt attacggctc ttattacact gacaatcagg gtaatttcta    2280
tgttcctggc aatgtcaatt gggaaaaccg tcgaattgtc gctaatcata acggcaagaa    2340
cattacatgg gaagatggtt ggggtttgtt agatccagaa gcggccgcta aaggttatgg    2400
tggtttctat tgggataatg tggaattaga cactaaaggc acgcctttat ctgtattcta    2460
caatgaccta aaaggtgata aaggctttac caaaaaaggt gaaggtaaac ttgtctttac    2520
tggtaataat agctataaag gcgactctgt catcgagggt ggttcactag aagtaaatgg    2580
taacaacggt ggttcaacca tggttgttaa aggtggtgaa ctaacaggtt atggtaatgt    2640
agctaatgtt cgtcaaacag gtggttgggt taacaacgaa ggtaacctaa acatcagagg    2700
tgactacaac atcaacactc aacgtggcgt ggatgctggt ctaaaagctc aatttggcaa    2760
catgcttacc gtggacggta aggccaaact aggtggtaca ctaaatctaa ctggtgagac    2820
caaagatggt atcatcagca aatcaggtag ccgtagcact gtacttcgtg ctaagcgtgg    2880
tcttgaaggt caatttgaca attatcgttc aagcaaccca ttatttgaag taacaaatgt    2940
tgaatatacg ccagaagtag acagaaatgg cagagtggta ggtggttcac gcacgaacaa    3000
tgacgtgcaa gtaactgcca aacgtctaag tgcaggcaat gttgtttatg catcagcat     3060 gaatgacagt ggtagccgtg ttgcacaaaa cctagacaaa gtacttaatg atttagataa    3120
aaaacaagaa acacaaggtt cactgaccag tgatgagaag caatttgcta accgtgtatt    3180
cactggtttt gaaaacatga attctggtgc agaatctaaa cttctacag taagcaccaa     3240 ccgtgagcta tacaagcttg acccaacttt ctatgctgac agtgcattaa acgcagtaga    3300
agacagtgct aaccatgcaa ccgaatttgg taagcgtgtt agcgccccaa gaggtgtttg    3360
gggtaatatc agtcaccatg attatgatgt agaactagag catgctacaa gtgcacgtaa    3420
aggcaacaac attagtgttg gtgcaagcac tcaaactgca gccgacatta gtgttggtgc    3480
acaacttgat gtaagtaaac ttgacttgga agaatctgtt tatggtattg gcaacaaaac    3540
caaaactgac agcattggct tgactgttgg tgcttctaag aagttgggtg atgcctatct    3600
atcaggttgg gtaaaaggtg ccaaagttga tacagaagcg aaccgtggtg aaaactctaa    3660
caaagttgag tacaatggta agctatatgg tgctggtatc caagcgggta caaacattga    3720
tactgcatcg gcgtgagtg tacaaccttg tgcctttgtt aaccatcagc agtacaaaaa      3780
cgatggtagc ttcaatgacg gtcttaacgt tgttgacgac atcgaagcaa acaaactca      3840 ggtaggtgtg ggtgctgata tggtgttcca agcaacacct gctctacagc ttactggtgg    3900
tgtgcaagtt gctcacgctg ttagccgtga caccaaccta gacactcgct atgttggtac    3960
agcgacagat gtacagtatg gcacttggga tactgacaaa accaaatggt cagccaaggt    4020
```

-continued

```
tggtgctaac tataatgtga caccaaacag ccaagtgggt ctaaactaca gctacacagg    4080
tagtggcgat tcagatgctt cccaagtggg tgtgagcttc accagcaagt tctaattcat    4140
taataaggca acaaaaaaca gcacaatttc ggttgtgctg ttttttgtga tgccgagcgt    4200
aaaattttcc caaaaaaagc gtgataatta ccacgctttt ttattgcata ttgcaaaata    4260
gtattgcatt tatgggttgt taagcaaccc gtccaaatac cccctaaaca actccacccc    4320
aatcggtgct aacttgtttt gccacaggct cgtcaatgtg tcggcatcat caaccattac    4380
cgac                                                                 4384
```

<210> SEQ ID NO 3
<211> LENGTH: 616
<212> TYPE: PRT
<213> ORGANISM: Moraxella bovis

<400> SEQUENCE: 3

```
Met Lys Lys Ser Ala Phe Ala Lys Tyr Ser Ala Leu Ala Leu Met Val
 1               5                  10                  15

Gly Met Cys Leu His Thr Ala Tyr Ala Lys Glu Phe Ser Gln Val Ile
             20                  25                  30

Ile Phe Gly Asp Ser Leu Ser Asp Thr Gly Arg Leu Lys Asp Met Val
         35                  40                  45

Ala Arg Lys Asp Gly Thr Leu Gly Asn Thr Leu Gln Pro Ser Phe Thr
     50                  55                  60

Thr Asn Pro Asp Pro Val Trp Ser Ser Leu Phe Ala Gln Ser Tyr Gly
 65                  70                  75                  80

Lys Thr Ala Ser Ala Asn Thr Pro Tyr Asn Pro Thr Gly Thr Asn Tyr
                 85                  90                  95

Ala Val Gly Gly Ala Arg Ser Gly Ser Glu Val Asn Trp Asn Gly Phe
            100                 105                 110

Val Asn Val Pro Ser Thr Lys Thr Gln Ile Thr Asp His Leu Thr Ala
        115                 120                 125

Thr Gly Gly Lys Ala Asp Pro Asn Thr Leu Tyr Ala Ile Trp Ile Gly
    130                 135                 140

Ser Asn Asp Leu Ile Ser Ala Ser Gln Ala Thr Thr Ala Glu Ala
145                 150                 155                 160

Gln Asn Ala Ile Lys Gly Ala Val Thr Arg Thr Val Ile Asp Ile Glu
                165                 170                 175

Thr Leu Asn Gln Ala Gly Ala Thr Thr Ile Leu Val Pro Asn Val Pro
            180                 185                 190

Asp Leu Ser Leu Thr Pro Arg Ala Ile Tyr Gly Glu Ser Leu Met Ala
        195                 200                 205

Gly Val Gln Asp Lys Ala Lys Leu Ala Ser Ser Leu Tyr Asn Ser Gly
    210                 215                 220

Leu Phe Glu Ala Leu Asn Gln Ser Thr Ala Asn Ile Ile Pro Ala Asn
225                 230                 235                 240

Thr Phe Ala Leu Leu Gln Glu Ala Thr Thr Asn Lys Glu Ala Phe Gly
                245                 250                 255

Phe Lys Asn Thr Gln Gly Val Ala Cys Gln Met Pro Ala Arg Thr Thr
            260                 265                 270

Gly Ala Asp Asp Val Ala Ser Thr Ser Leu Ala Cys Thr Lys Ala Asn
        275                 280                 285

Leu Ile Glu Asn Gly Ala Asn Asp Thr Tyr Ala Phe Ala Asp Asp Ile
    290                 295                 300
```

-continued

```
His Pro Ser Gly Arg Thr His Arg Ile Leu Ala Gln Tyr Tyr Arg Ser
305                 310                 315                 320

Ile Met Asp Ala Pro Thr His Met Gly Lys Leu Ser Gly Glu Leu Val
                325                 330                 335

Lys Thr Gly Ser Ala His Asp Arg His Val Tyr Arg Gln Leu Asp Arg
            340                 345                 350

Leu Ser Gly Ser Gln His Ser Ile Trp Ala Asn Val His Ala Ser Asp
        355                 360                 365

Arg Thr Asp Pro Thr Thr Gln Ile Gly Leu Asp Val Ala Gly Ser Ser
    370                 375                 380

Ser His Thr Gly Ala Tyr Leu Ser His Gln Asn Gln Asp Tyr Val Leu
385                 390                 395                 400

Asp Asp Thr Leu Ser Ser Asp Val Lys Thr Ile Gly Met Gly Leu Tyr
                405                 410                 415

His Arg His Asp Ile Gly Asn Val Arg Leu Lys Gly Val Ala Gly Ile
            420                 425                 430

Asp Arg Leu Ser Val Asp Thr His Arg His Ile Asp Trp Glu Gly Ala
        435                 440                 445

Ser Arg Ser His Thr Ala Asp Thr Thr Ala Arg Arg Phe His Ala Gly
    450                 455                 460

Leu Gln Ala Ser Tyr Gly Ile Asp Met Gly Lys Ala Thr Val Arg Pro
465                 470                 475                 480

Leu Ile Gly Val His Ala Gln Lys Val Lys Val Arg Asp Leu Val Glu
                485                 490                 495

Asn Glu Pro Thr Leu Ser Thr Ala Met Arg Phe Gly Glu Gln Glu Gln
            500                 505                 510

Lys Ser Leu Gln Gly Glu Ile Gly Val Asp Val Ala Tyr Pro Ile Ser
        515                 520                 525

Pro Ala Leu Thr Leu Thr Gly Gly Ile Ala His Ala His Glu Phe Asn
    530                 535                 540

Asp Asp Glu Arg Thr Ile Asn Ala Thr Leu Thr Ser Ile Arg Glu Tyr
545                 550                 555                 560

Thr Lys Gly Phe Asn Thr Ser Val Ser Thr Asp Lys Ser His Ala Thr
                565                 570                 575

Thr Ala His Leu Gly Val Gln Gly Gln Leu Gly Lys Ala Asn Ile His
            580                 585                 590

Ala Gly Val His Ala Thr His Gln Asp Ser Asp Thr Asp Val Gly Gly
        595                 600                 605

Ser Leu Gly Val Arg Leu Met Phe
    610                 615
```

<210> SEQ ID NO 4
<211> LENGTH: 2110
<212> TYPE: DNA
<213> ORGANISM: Moraxella bovis

<400> SEQUENCE: 4

```
tgacaaataa ttgggcattg ggcagataac ccatcaaaga cccaaagcaa cccataaatc     60
aaaaaaacac ttgtaatttt tgtaatatct tgttacactt tacaagtgtt tttactttga    120
aagcaactca gagagtaata atgaaaaaat ccgcctttgc caaatactca gcacttgccc    180
taatggttgg gatgtgcctg cacaccgctt acgccaagga gtttagccaa gtcatcattt    240
ttggggacag cttgtccgat acaggtcgcc taaaagatat ggtcgcccga aaagatggca    300
```

-continued

```
cccttggcaa caccttacag ccatcttta ccaccaaccc cgaccctgta tggtcaagct      360
tatttgccca agttatggc aaaaccgcca gtgccaacac gccctacaat cccactggca      420
ctaactatgc cgtgggcgga gctcgctctg gctcggaggt caattggaat ggttttgtga    480
atgtaccctc caccaaaacg caaatcaccg accatttgac cgccacaggt ggcaaagccg    540
accctaatac cctgtatgcc atttggattg gctctaatga cttaatttca gcttctcaag    600
ccaccacaac agccgaagcc caaaacgcca ttaaaggtgc ggtaactcgc accgtgatag    660
acatcgaaac actcaatcaa gcagggcgca caaccatttt ggtgccaaat gtgcctgatt    720
tgagcctcac gccccgagcc atctatggcg aaagcctcat ggcaggcgtg caagacaaag    780
ccaaactcgc ctcaagtctg tataatagcg gtctgtttga agcattaaat caatccaccg    840
ccaacatcat ccctgccaac acctttgccc tactccaaga agcgaccaca aataagaag    900
cctttggttt taaaaacacg caaggcgtgg cgtgtcaaat gcccgctcgt accacagggg    960
cggatgatgt ggcttctact tccttggcat gtaccaaagc caatcttata gaaaacgggg  1020
caaatgacac ctacgccttt gccgatgaca ttcacccatc gggacgcacg caccgcattt  1080
tggcacagta ttaccgttct atcatggacg cccctactca catgggtaaa ctctcaggcg  1140
agcttgtcaa acaggttca gcccacgacc gtcatgttta ccgtcagctt gacaggctta  1200
gtggctcaca gcacagcatt tgggcaaacg tccatgccag cgaccgtacc gaccccacca  1260
cccaaatcgg cttggacgtg gcaggttcat caagccatac agggcgtat ctgagccacc  1320
aaaaccaaga ttatgtgctg gatgacaccc tatcatcaga tgtcaaaacc attggcatgg  1380
ggctgtatca tcgccatgac atcggcaatg tccgtctaaa aggcgtggca ggtatcgacc  1440
gacttagcgt ggatacgcac cgccatatcg actgggaggg ggcaagccgt tcgcacacgg  1500
cagacaccac cgccagacgt tttcatgcag ggctacaagc cagctatggc atagacatgg  1560
gcaaagccac cgtgcgtccg cttatcggcg tacatgccca aaaagtcaaa gtgcgtgatt  1620
tggtagagaa tgagcctacc ctatccaccg ccatgcgttt tggcgagcaa gaacaaaagt  1680
ccctacaagg cgagattggc gtcgatgtgg cttatccgat tagccctgct ttgactctga  1740
cgggcggtat cgctcacgct catgagttta acgatgatga acgcaccatt aatgccactt  1800
taacctccat tcgtgaatac acgaagggct ttaatacaag cgttagcacc gacaaatctc  1860
acgccaccac cgctcatctg ggcgtacaag ggcaacttgg caaggcaaat attcatgcag  1920
gcgttcacgc cacccaccaa gacagcgata cagacgtggg tggttcgctt ggggttcgct  1980
tgatgttttg attggctttt aaagataaaa agtggtatca tgccactttt tattttgcca  2040
aaaatctatg tttgagtaca tcaaagcctt tcacatcatc gccatgcgat gataagctgt  2100
caaacatgag                                                          2110
```

<210> SEQ ID NO 5
<211> LENGTH: 927
<212> TYPE: PRT
<213> ORGANISM: Moraxella bovis

<400> SEQUENCE: 5

```
Met Ser Asn Ile Asn Val Ile Lys Ser Asn Ile Gln Ala Gly Leu Asn
  1               5                  10                  15

Ser Thr Lys Ser Gly Leu Lys Asn Leu Tyr Leu Ala Ile Pro Lys Asp
             20                  25                  30

Tyr Asp Pro Gln Lys Gly Gly Thr Leu Asn Asp Phe Ile Lys Ala Ala
         35                  40                  45
```

-continued

```
Asp Glu Leu Gly Ile Ala Arg Leu Ala Glu Glu Pro Asn His Thr Glu
     50                  55                  60
Thr Ala Lys Lys Ser Val Asp Thr Val Asn Gln Phe Leu Ser Leu Thr
 65                  70                  75                  80
Gln Thr Gly Ile Ala Ile Ser Ala Thr Lys Leu Glu Lys Phe Leu Gln
                 85                  90                  95
Lys His Ser Thr Asn Lys Leu Ala Lys Gly Leu Asp Ser Val Glu Asn
                100                 105                 110
Ile Asp Arg Lys Leu Gly Lys Ala Ser Asn Val Leu Ser Thr Leu Ser
            115                 120                 125
Ser Phe Leu Gly Thr Ala Leu Ala Gly Ile Glu Leu Asp Ser Leu Ile
    130                 135                 140
Lys Lys Gly Asp Ala Ala Pro Asp Ala Leu Ala Lys Ala Ser Ile Asp
145                 150                 155                 160
Leu Ile Asn Glu Ile Ile Gly Asn Leu Ser Gln Ser Thr Gln Thr Ile
                165                 170                 175
Glu Ala Phe Ser Ser Gln Leu Ala Lys Leu Gly Ser Thr Ile Ser Gln
            180                 185                 190
Ala Lys Gly Phe Ser Asn Ile Gly Asn Lys Leu Gln Asn Leu Asn Phe
        195                 200                 205
Ser Lys Thr Asn Leu Gly Leu Glu Ile Ile Thr Gly Leu Leu Ser Gly
210                 215                 220
Ile Ser Ala Gly Phe Ala Leu Ala Asp Lys Asn Ala Ser Thr Gly Lys
225                 230                 235                 240
Lys Val Ala Ala Gly Phe Glu Leu Ser Asn Gln Val Ile Gly Asn Val
                245                 250                 255
Thr Lys Ala Ile Ser Ser Tyr Val Leu Ala Gln Arg Val Ala Ala Gly
            260                 265                 270
Leu Ser Thr Thr Gly Ala Val Ala Ala Leu Ile Thr Ser Ser Ile Met
        275                 280                 285
Leu Ala Ile Ser Pro Leu Ala Phe Met Asn Ala Ala Asp Lys Phe Asn
    290                 295                 300
His Ala Asn Ala Leu Asp Glu Phe Ala Lys Gln Phe Arg Lys Phe Gly
305                 310                 315                 320
Tyr Asp Gly Asp His Leu Leu Ala Glu Tyr Gln Arg Gly Val Gly Thr
                325                 330                 335
Ile Glu Ala Ser Leu Thr Thr Ile Ser Thr Ala Leu Gly Ala Val Ser
            340                 345                 350
Ala Gly Val Ser Ala Ala Val Gly Ser Ala Val Gly Thr Pro Ile
        355                 360                 365
Ala Leu Leu Val Ala Gly Val Thr Gly Leu Ile Ser Gly Ile Leu Glu
    370                 375                 380
Ala Ser Lys Gln Ala Met Phe Glu Ser Val Ala Asn Arg Leu Gln Gly
385                 390                 395                 400
Lys Ile Leu Glu Trp Glu Lys Gln Asn Gly Gly Gln Asn Tyr Phe Asp
                405                 410                 415
Lys Gly Tyr Asp Ser Arg Tyr Ala Ala Tyr Leu Ala Asn Asn Leu Lys
            420                 425                 430
Phe Leu Ser Glu Leu Asn Lys Glu Leu Glu Ala Glu Arg Val Ile Ala
        435                 440                 445
Ile Thr Gln Gln Arg Trp Asp Asn Asn Ile Gly Glu Leu Ala Gly Ile
    450                 455                 460
Thr Lys Leu Gly Glu Arg Ile Lys Ser Gly Lys Ala Tyr Ala Asp Ala
```

-continued

```
465                 470                 475                 480
Phe Glu Asp Gly Lys Lys Val Glu Ala Gly Ser Asn Ile Thr Leu Asp
                485                 490                 495
Ala Lys Thr Gly Ile Ile Asp Ile Ser Asn Ser Asn Gly Lys Lys Thr
                500                 505                 510
Gln Ala Leu His Phe Thr Ser Pro Leu Leu Thr Ala Gly Thr Glu Ser
                515                 520                 525
Arg Glu Arg Leu Thr Asn Gly Lys Tyr Ser Tyr Ile Asn Lys Leu Lys
                530                 535                 540
Phe Gly Arg Val Lys Asn Trp Gln Val Thr Asp Gly Glu Ala Ser Ser
545                 550                 555                 560
Lys Leu Asp Phe Ser Lys Val Ile Gln Arg Val Ala Glu Thr Glu Gly
                565                 570                 575
Thr Asp Glu Ile Gly Leu Ile Val Asn Ala Lys Ala Gly Asn Asp Asp
                580                 585                 590
Ile Phe Val Gly Gln Gly Lys Met Asn Ile Asp Gly Gly Asp Gly His
                595                 600                 605
Asp Arg Val Phe Tyr Ser Lys Asp Gly Phe Gly Asn Ile Thr Val
                610                 615                 620
Asp Gly Thr Ser Ala Thr Glu Ala Gly Ser Tyr Thr Val Asn Arg Lys
625                 630                 635                 640
Val Ala Arg Gly Asp Ile Tyr His Glu Val Lys Arg Gln Glu Thr
                645                 650                 655
Lys Val Gly Lys Arg Thr Glu Thr Ile Gln Tyr Arg Asp Tyr Glu Leu
                660                 665                 670
Arg Lys Val Gly Tyr Gly Tyr Gln Ser Thr Asp Asn Leu Lys Ser Val
                675                 680                 685
Glu Glu Val Ile Gly Ser Gln Phe Asn Asp Val Phe Lys Gly Ser Lys
                690                 695                 700
Phe Asn Asp Ile Phe His Ser Gly Glu Gly Asp Leu Leu Asp Gly
705                 710                 715                 720
Gly Ala Gly Asp Asp Arg Leu Phe Gly Gly Lys Gly Asn Asp Arg Leu
                725                 730                 735
Ser Gly Asp Glu Gly Asp Asp Leu Leu Asp Gly Gly Ser Gly Asp Asp
                740                 745                 750
Val Leu Asn Gly Gly Ala Gly Asn Asp Val Tyr Ile Phe Arg Lys Gly
                755                 760                 765
Asp Gly Asn Asp Thr Leu Tyr Asp Gly Thr Gly Asn Asp Lys Leu Ala
                770                 775                 780
Phe Ala Asp Ala Asn Ile Ser Asp Ile Met Ile Glu Arg Thr Lys Glu
785                 790                 795                 800
Gly Ile Ile Val Lys Arg Asn Asp His Ser Gly Ser Ile Asn Ile Pro
                805                 810                 815
Arg Trp Tyr Ile Thr Ser Asn Leu Gln Asn Tyr Ser Asn Lys Thr
                820                 825                 830
Asp His Lys Ile Glu Gln Leu Ile Gly Lys Asp Gly Ser Tyr Ile Thr
                835                 840                 845
Ser Asp Gln Ile Asp Lys Ile Leu Gln Asp Lys Lys Asp Gly Thr Val
                850                 855                 860
Ile Thr Ser Gln Glu Leu Lys Lys Leu Ala Asp Glu Asn Lys Ser Gln
865                 870                 875                 880
Lys Leu Ser Ala Ser Asp Ile Ala Ser Ser Leu Asn Lys Leu Val Gly
                885                 890                 895
```

```
Ser Met Ala Leu Phe Gly Thr Ala Asn Ser Val Ser Ser Asn Ala Leu
        900                 905                 910
Gln Pro Ile Thr Gln Pro Thr Gln Gly Ile Leu Ala Pro Ser Val
        915                 920                 925

<210> SEQ ID NO 6
<211> LENGTH: 3231
<212> TYPE: DNA
<213> ORGANISM: Moraxella bovis

<400> SEQUENCE: 6
atgagaacgt tattttcaga tgaattgttt agagcgattc gtgtagatgg aaattcatcg      60
catggtaaga tatctgaatt ttatggaaag tctgttgatt caaaattagc ctcaagaata     120
tttgcacaat atcacgaaga tttgacgagc aaattgtcaa ctcagaataa ttttattata     180
tctaaagata ttaatacaa cctttttctaa cacaacgagg agagacatat tatgtccaat     240
ataaatgtaa ttaaatctaa tattcaagca ggcttgaatt caacaaagtc tggattaaaa     300
aatctttact tggctattcc caaagattat gatccgcaaa aggtgggac tttaaatgat      360
tttattaaag ctgctgatga attaggtatt gctcgtttag cagaagagcc taatcacact     420
gaaacagcaa aaaatctgt tgacacagta atcagtttc tctctctcac acaaactggt       480
attgctattt ctgcaacaaa attagaaaag ttcttacaaa acattctac caataagtta     540
gccaaagggt tagacagtgt agaaaatatt gatcgtaaat taggtaaagc aagtaatgta     600
ttatcaacat taagctcttt tttgggcact gcattagcgg gtatagaact tgattcttta     660
atcaaaaaag gtgatgctgc acctgatgct ttggctaaag ctagtattga cttgattaat     720
gagataattg gtaatctatc tcagagtact caaacgattg aagcattttc ttcacagtta     780
gcaaagttag gttctactat atcgcaggct aaaggcttct ctaatatagg aaacaagttg     840
caaaacttaa attttctaa acaaatctt ggtttggaaa taattactgg tttgctatca        900
ggcatttctg caggctttgc tttagcggat aaaaatgcat cgactggcaa aaaagttgct     960
gcaggttttg aattaagcaa tcaagttatt ggtaatgtaa caaagcaat tcttcatat       1020
gttttagcac aacgtgttgc tgctggtcta tcaactactg gtgctgttgc tgctttaatt   1080
acttcatcga ttatgttggc aattagtcct ttggcattta tgaatgcagc agataaattc   1140
aatcatgcta atgctcttga tgagtttgca aaacaattcc gaaaatttgg ctatgatggg   1200
gatcatttat tggctgaata tcagcgtggt gtgggtacta ttgaagcttc attaactaca   1260
attagtacgg cattaggtgc agtttctgct ggtgtttccg ctgctgctgt aggatctgct   1320
gttggtacac cgattgcact attagttgca ggtgttacag gattgatctc tggaattta    1380
gaagcgtcta acaggcaat gtttgaaagt gttgctaacc gtttacaagg taaaatttta    1440
gagtgggaaa agcaaaatgg cggtcagaac tattttgata aggctatga ttctcgttat    1500
gctgcttatt tagctaataa cttaaaattt ttgtctgagc taaataaaga gttggaagct   1560
gaacgtgtta ttgcaatcac ccaacaacgt tgggataata tattggtga ttagcaggt     1620
attaccaaat tgggtgaacg cattaagagc ggaaaagctt atgcagatgc ttttgaagat   1680
ggcaagaaag ttgaagctgg ttccaatatt actttggatg ctaaaactgg tatcatagac   1740
attagtaatt caaatgggaa aaaaacgcaa gcgttgcatt tcacttcgcc tttgttaaca   1800
gcaggaactg aatcacgtga acgttttaact aatggtaaat actcttatat taataagtta   1860
aaattcggac gtgtaaaaaa ctggcaagtt acagatggag aggctagttc taaattagat   1920
```

-continued

```
ttctctaaag ttattcagcg tgtagccgag acagaaggca cagacgagat tggtctaata    1980
gtaaatgcaa aagctggcaa tgacgatatc tttgttggtc aagtaaaaat gaatattgat    2040
ggtggagatg gacacgatcg tgtcttctat agtaaagacg gaggatttgg taatattact    2100
gtagatggta cgagtgcaac agaagcaggc agttatacag ttaatcgtaa ggttgctcga    2160
ggtgatatct accatgaagt tgtgaagcgt caagaaacca aggtgggtaa acgtactgaa    2220
actatccagt atcgtgatta tgaattaaga aaagttgggt atggttatca gtctaccgat    2280
aatttgaaat cagtagaaga agtaattggt tctcaattta atgatgtatt caaaggttct    2340
aaattcaacg acatattcca tagtggtgaa ggtgatgatt actcgatgg tggtgctggt    2400
gacgaccgct tgtttggtgg taaaggcaac gatcgacttt ctggagatga aggcgatgat    2460
ttactcgatg gcggttctgg tgatgatgta ttaaatggtg gtgctggtaa tgatgtctat    2520
atctttcgga aggtgatgg taatgatact ttgtacgatg gcacgggcaa tgataaatta    2580
gcatttgcag atgcaaatat atctgatatt atgattgaac gtaccaaaga gggtattata    2640
gttaaacgaa atgatcattc aggtagtatt aacataccaa gatggtacat aacatcaaat    2700
ttacaaaatt atcaaagtaa taaaacagat cataaaattg agcaactaat tggtaaagat    2760
ggtagttata tcacttccga tcaaattgat aaaattttgc aagataagaa agatggtaca    2820
gtaattacat ctcaagaatt gaaaaagctt gctgatgaga ataagagcca aaaattatct    2880
gcttcggaca ttgcaagtag cttaaataag ctagttgggt caatggcact atttggtaca    2940
gcaaatagtg tgagttctaa cgccttacag ccaattacac aaccaactca aggaattttg    3000
gctccaagtg tttagtgatt taatttacta gacaatatca ccacccatat cattggttat    3060
agattatgaa actagtgata tgggtggtga tacttcttta attagactta atttacaaac    3120
ccttaatagt aatttagtta tgatagatta tgctcaacaa cctgctctat ctgctctggt    3180
tatccttgcc aaatactatg gtatttctgc aagtccagca gacattatgc a             3231
```

<210> SEQ ID NO 7
<211> LENGTH: 17
<212> TYPE: PRT
<213> ORGANISM: Moraxella bovis
<220> FEATURE:
<221> NAME/KEY: misc_feature
<222> LOCATION: (14)(16)
<223> OTHER INFORMATION: Xaa = unsure

<400> SEQUENCE: 7

Lys Glu Phe Ser Gln Val Ile Ile Phe Gly Asp Ser Leu Xaa Asp Xaa
 1               5                  10                  15

Gly

<210> SEQ ID NO 8
<211> LENGTH: 64
<212> TYPE: PRT
<213> ORGANISM: Moraxella bovis

<400> SEQUENCE: 8

Met Arg Thr Leu Phe Ser Asp Glu Leu Phe Arg Ala Ile Arg Val Asp
 1               5                  10                  15

Gly Asn Ser Ser His Gly Lys Ile Ser Glu Phe Tyr Gly Lys Ser Val
                20                  25                  30

Asp Ser Lys Leu Ala Ser Arg Ile Phe Ala Gln Tyr His Glu Asp Leu
        35                  40                  45

Thr Ser Lys Leu Ser Thr Gln Asn Asn Phe Ile Ile Ser Lys Asp Asn

```
                    50                  55                  60

<210> SEQ ID NO 9
<211> LENGTH: 57
<212> TYPE: PRT
<213> ORGANISM: Moraxella bovis

<400> SEQUENCE: 9

Met Gly Gly Asp Thr Ser Leu Ile Arg Leu Asn Leu Gln Thr Leu Asn
 1               5                  10                  15

Ser Asn Leu Val Met Ile Asp Tyr Ala Gln Gln Pro Ala Leu Ser Ala
            20                  25                  30

Leu Val Ile Leu Ala Lys Tyr Tyr Gly Ile Ser Ala Ser Pro Ala Asp
        35                  40                  45

Ile Met His Arg Leu Ala Lys Lys Leu
        50                  55
```

VACCINE ANTIGENS OF *MORAXELLA*

CROSS REFERENCE TO RELATED APPLICATIONS

This application is a National Stage Application of PCT International Application No. PCT/AU00/01048, filed on Aug. 31, 2000 which claims priority to Australian Patent Application No. PQ2571, filed on Aug. 31, 1999, both of which are incorporated herein, by reference, in their entirety.

FIELD OF THE INVENTION

The present invention relates to antigens of *Moraxella*, in particular, *Moraxella bovis*, nucleic acid sequences encoding these antigens and formulations for use in raising an immune response against *Moraxella*.

BACKGROUND OF THE INVENTION

Infectious bovine keratoconjunctivitis (IBK) is an economically important disease of cattle caused by the Gram-negative coccobacillus *Moraxella bovis*. More commonly known as pinkeye, IBK is a highly contagious ocular infection which may range from mild conjunctivitis to severe ulceration, corneal perforation and blindness. Therapeutic and preventative measures have limited success in controlling IBK and a vaccine which will prevent the disease is required. A number of factors contribute to the virulence of the organism, the two most important attributes so far identified are the expression of pili, and the ability to produce haemolysin. Seven different serogroups of *M. bovis* strains isolated in Australia, Great Britain and the USA have been characterised, based on pilus types (1). An efficacious pilus-based vaccine must contain a sufficient quantity of pili from all seven serotypes to be fully protective, because of a lack of cross protection between serotypes (2, 3). Expression of all seven pilus serotypes at levels high enough to be useful for commercial vaccine preparation has not been achieved.

The ideal vaccine candidate to stimulate protection against *M. bovis* would be a molecule that is highly-conserved among all strains of this species. Possible candidates are haemolysin, protease, lipase and/or phospholipase (4) enzymes produced by *M. bovis*. For example, a partially purified cell-free supernatant from one haemolytic strain of *M. bovis* has been shown to confer significant protection against heterologous, wild-type challenge (5). The possibility that a haemolysin could be conserved across all seven serotypes of *M. bovis* makes it a potential vaccine candidate against IBK. However, researchers have so far been unable to either clone the gene encoding the haemolysin or purify the protein to homogeneity. Nevertheless, any or all of these molecules, alone or in combination, could prove useful for the generation of an effective vaccine against IBK.

SUMMARY OF THE INVENTION

In a first aspect the present invention consists in a polypeptide, the polypeptide having an amino acid sequence as set out in SEQ. ID. NO. 1 from amino acid 37 to 1114, or a sequence having at least 50% identity thereto, or a functional fragment thereof.

In a preferred embodiment the polypeptide has a sequence of at least 70%, more preferably at least 80% and most preferably at least 90% identity with the sequence shown in SEQ. ID. NO. 1.

In a further preferred embodiment of the first aspect of the present invention the polypeptide has protease activity.

In a second aspect the present invention consists in a nucleic acid molecule, the nucleic acid molecule encoding the polypeptide of the first aspect of the present invention.

In a third aspect the present invention consists in a nucleic acid molecule comprising a sequence as set out in SEQ. ID. NO. 2 or a sequence having at least 60% identity thereto, or a sequence which hybridises thereto under stringent conditions.

In a preferred embodiment the nucleic acid molecule has a sequence of at least 70%, more preferably at least 80% and most preferably at least 90% identity with the sequence shown in SEQ. ID. NO. 2.

In a fourth aspect the present invention consists in a composition for use in raising an immune response in an animal, the composition comprising the polypeptide of the first aspect of the present invention or the nucleic acid sequence of the second aspect of the present invention and optionally a carrier and/or adjuvant.

In a fifth aspect the present invention consists in a polypeptide, the polypeptide having an amino acid sequence as set out in SEQ. ID. NO. 3 from amino acid 26 to 616, or a sequence having at least 50% identity thereto, or a functional fragment thereof.

In a preferred embodiment the polypeptide has a sequence of at least 70%, more preferably at least 80% and most preferably at least 90% identity with the sequence shown in SEQ. ID. NO. 3 from amino acid 26 to 616.

In a further preferred embodiment of the fifth aspect the polypeptide has lipase activity.

In a sixth aspect the present invention consists in a nucleic acid molecule, the nucleic acid molecule encoding the polypeptide of the fifth aspect of the present invention.

In a seventh aspect the present invention consists in a nucleic acid molecule comprising a sequence as set out in SEQ. ID. NO. 4 or a sequence having at least 60% identity thereto, or a sequence which hybridises thereto under stringent conditions.

In a preferred embodiment the nucleic acid molecule has a sequence of at least 70%, more preferably at least 80% and most preferably at least 90% identity with the sequence shown in SEQ. ID. NO. 4.

In an eighth aspect the present invention consists in a composition for use in raising an immune response in an animal, the composition comprising the polypeptide of the fifth aspect of the present invention or the nucleic acid sequence of the sixth aspect of the present invention and optionally a carrier and/or adjuvant.

In a ninth aspect the present invention consists in a polypeptide, the polypeptide having an amino acid sequence as set out in SEQ. ID. NO. 5, or a sequence having at least 60% identity thereto, or a functional fragment thereof.

In a preferred embodiment the polypeptide has a sequence of at least 70%, more preferably at least 80% and most preferably at least 90% identity with the sequence shown in SEQ. IID. NO. 5.

In a further preferred embodiment of the ninth aspect the polypeptide has haemolysin activity.

In a tenth aspect the present invention consists in a nucleic acid molecule, the nucleic acid molecule encoding the polypeptide of the ninth aspect of the present invention.

In an eleventh aspect the present invention consists in a nucleic acid molecule comprising a sequence as set out in SEQ. ID. NO. 6 or a sequence having at least 60% identity thereto, or a sequence which hybridises thereto under stringent conditions.

In a preferred embodiment the nucleic acid molecule has a sequence of at least 70%, more preferably at least 80% and most preferably at least 90% identity with the sequence shown in SEQ. ID. NO. 6.

In a twelfth aspect the present invention consists in a composition for use in raising an immune response in an animal, the composition comprising the polypeptide of the ninth aspect of the present invention or the nucleic acid sequence of the tenth aspect of the present invention and optionally a carrier and/or adjuvant.

The term "functional fragment" as used herein is intended to cover fragments of the polypeptide which retain at least 10% of the biological activity of the complete polypeptide. In particular this term is used to encompass fragments which show immunological cross-reactivity with the entire polypeptide, eg ligands which react with the fragment also react with the complete polypeptide.

In a thirteenth aspect the present invention consists in a composition for use in raising an immune response in an animal directed against *Moraxella*, the composition comprising at least one polypeptide selected from the group consisting of the polypeptides of the first, fifth and ninth aspects of the present invention and optionally including an adjuvant or carrier.

In a preferred embodiment the composition includes the polypeptide of the ninth aspect of the present invention and either one of, or preferably both, the polypeptides of the first and fifth aspects of the present invention.

In a preferred embodiment the *Moraxella* is *M. bovis* or *M. catarrhalis*, most preferably *M. bovis*.

In a fourteenth aspect the present invention consists in an antibody raised against a polypeptide selected from the group consisting of the polypeptides of the first, fifth and ninth aspects.

As will be readily appreciated by the person skilled in this field the polypeptides and antibodies of the present invention and probes derived from the nucleotide sequences can be used as diagnostic reagents in determining *Moraxella*, in particular, *M. bovis* infection. For example, the polypeptides and antibodies can be used in ELISA based assays whilst the probes can be used in PCR based assays. The probes will be of a length to provide the required level of specificity and will typically be at least 18 nucleotides in length.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE FIGURES

Figure 1:
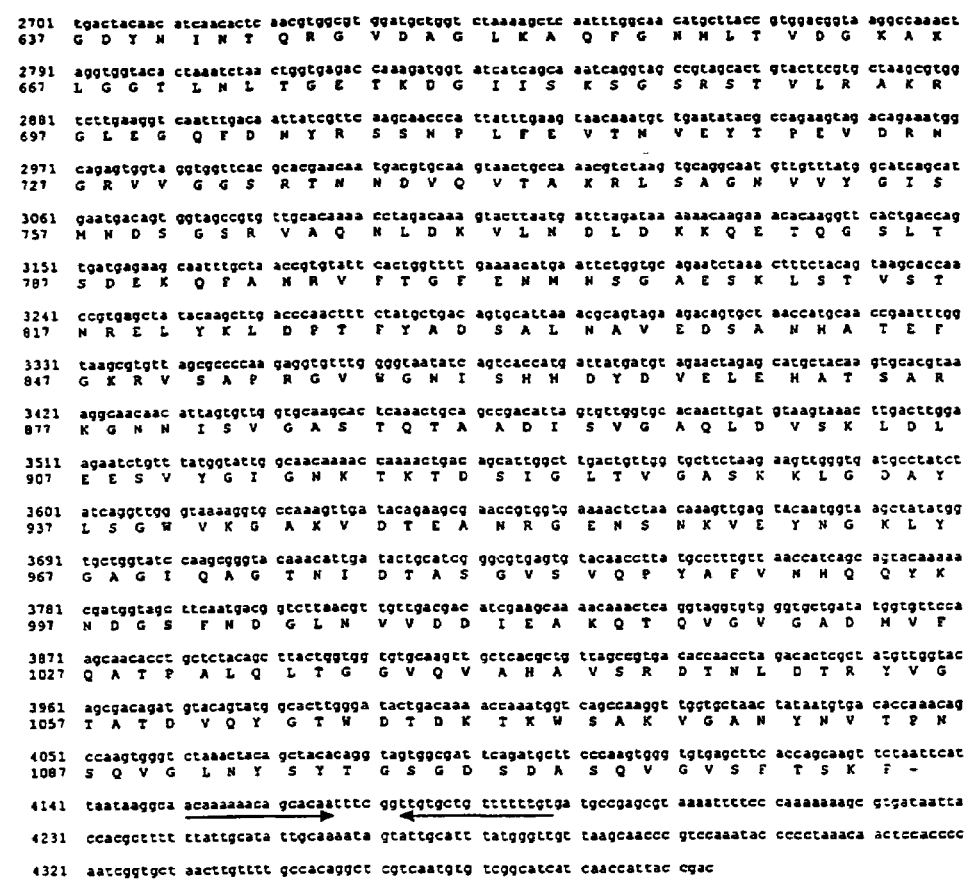

FIG. 1: Nucleotide and amino acid sequence of a protease from *M. bovis* Dalton 2 d. A putative promoter sequence is singly underlined. A putative ribosome binding site is shown in bold and underlined. A putative start codon is shown in bold. Putative transcription terminator sequences are indicated by inverted arrows. Numbering for both the nucleotide and amino acid sequences are shown on the left hand side.

FIG. 2: Nucleotide and amino acid sequence of a lipase from *M. bovis* Dalton 2 d. A putative promoter sequence is singly underlined. A putative ribosome binding site is shown in bold and underlined. A putative start codon is shown in bold. Putative transcription terminator sequences are indicated by inverted arrows. Numbering for both the nucleotide and amino acid sequences are shown on the left hand side.

FIG. 4: Comparison of growth rate and expression levels of the lipase of *M. bovis* when in its (i) native form and (ii) recombinant form. The growth rate is shown as solid bars and the lipase expression levels as open diamonds.

FIG. 5: Nucleotide and amino acid sequence of the A subunit of the RTX toxin from *M. bovis* Dalton 2 d. A putative ribosome binding site is shown in bold and underlined. A putative start codon is shown in bold. Upstream of the A subunit open reading frame is a portion of the coding region for the C subunit (nucleotide 1 to 195) (corresponding amino acid sequence shown in SEQ ID NO:8) and downstream of the A subunit is a small portion of the B subunit coding region (nucleotide 3080 to 3250) (corresponding amino acid sequence shown in SEQ ID NO:9). Numbering for both the nucleotide and amino acid sequences are shown on the left hand side.

DETAILED DESCRIPTION OF THE INVENTION

Figure 3:
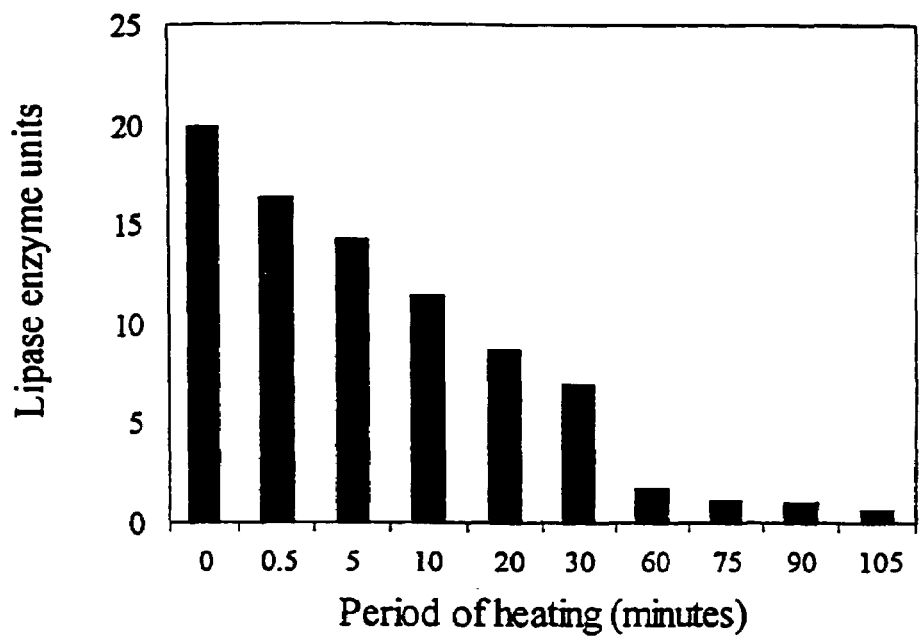
FIG. 3: Heat stability of the lipase from *M. bovis* when expressed in its recombinant form (pMB1/MC1061). (Heating carried out at 90° C.).

In order that the nature of the present invention may be more clearly understood preferred forms thereof will now be described with reference to the following non-limiting Examples.

General Molecular Biology

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1–4, IRL Press (1995 and 1996), and F. M. Ausubel et al. (Editors), Current Protocols in Molecular Biology, Greene Pub. Associates and Wiley-Interscience (1988, including all updates until present) and are incorporated herein by reference.

Protein Variants

Amino acid sequence variants can be prepared by introducing appropriate nucleotide changes into DNA, or by in vitro synthesis of the desired polypeptide. Such variants include, for example, deletions, insertions or substitutions of residues within the amino acid sequence. A combination of deletion, insertion and substitution can be made to arrive at the final construct, provided that the final protein product possesses the desired characteristics. The amino acid changes also may alter post-translational processes such as altering the membrane anchoring characteristics, altering the intra-cellular location by inserting, deleting or otherwise affecting the transmembrane sequences of the native protein, or modifying its susceptibility to proteolytic cleavage.

In designing amino acid sequence variants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of other ligands adjacent to the located site.

A useful method for identification of residues or regions for mutagenesis is called "alanine scanning mutagenesis" as described by Cunningham and Wells (*Science* (1989) 244: 1081–1085). Here, a residue or group of target residues are identified (e.g., charged residues such as Arg. Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants. Thus, while the site for introducing an amino acid sequence variation is predetermined, the nature of the mutation per se need not be predetermined. For example, to optimise the performance of a mutation at a given site, alanine scanning or random mutagenesis may be conducted at the target codon or region and the expressed variants are screened for the optimal combination of desired activity.

There are two principal variables in the construction of amino acid sequence variants; the location of the mutation site and the nature of the mutation. These may represent naturally occurring alleles or predetermined mutant forms made by mutating the DNA either to arrive at an allele or a variant not found in nature. In general, the location and nature of the mutation chosen will depend upon the characteristic to be modified.

Amino acid sequence deletions generally range from about 1 to 30 residues, more preferably about 1 to 10 residues and typically about 1 to 5 contiguous residues.

Amino acid sequence insertions include amino and/or carboxyl-terminal fusions ranging in length from one residue to polypeptides containing a hundred or more residues, as well as intrasequence insertions of single or multiple amino acid residues. Other insertional variants include the fusion of the N- or C-terminus of the proteins to an immunogenic polypeptide e.g. bacterial polypeptides such as betalactamase or an enzyme encoded by the *E. coli* trp locus, or yeast protein, bovine serum albumin, and chemotactic polypeptides. C-terminal fusions with proteins having a long half-life such as immunoglobulin constant regions (or other immunoglobulin regions), albumin, or ferritin, are included.

Another group of variants are amino acid substitution variants. These variants have at least one amino acid residue in the protein molecule removed and a different residue inserted in its place. The sites of greatest interest for substitutional mutagenesis include sites identified as the active site(s). Other sites of interest are those in which particular residues obtained from various species are identical. These positions may be important for biological activity. These sites, especially those falling within a sequence of at least three other identically conserved sites, are substituted in a relatively conservative manner. Such conservative substitutions are shown in Table 1 under the heading of "preferred substitutions". If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |

TABLE 1-continued

| Original Residue | Exemplary Substitutions | Preferred Substitutions |
| --- | --- | --- |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine, ile; val; met; ala; phe | ile |
| Lys (K) | arg; gln; asn | arg |
| Met (M) | leu; phe; ile; | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Mutants, Variants and Homology—Proteins

Mutant polypeptides will possess one or more mutations which are deletions, insertions, or substitutions of amino acid residues. Mutants can be either naturally occurring (that is to say, purified or isolated from a natural source) or synthetic (for example, by performing site-directed mutagensis on the encoding DNA). It is thus apparent that polypeptides of the invention can be either naturally occurring or recombinant (that is to say prepared using recombinant DNA techniques).

An allelic variant will be a variant that is naturally occurring within an individual organism.

Protein sequences are homologous if they are related by divergence from a common ancestor. Consequently, a species homologue of the protein will be the equivalent protein which occurs naturally in another species. Within any one species a homologue may exist as numerous allelic variants, and these will be considered homologues of the protein. Allelic variants and species homologues can be obtained by following standard techniques known to those skilled in the art. Preferred species homologues include those obtained from representatives of the same Phylum, more preferably the same Class and even more preferably the same Order.

A protein at least 50% identical, as determined by methods well known to those skilled in the art (for example, the method described by Smith, T. F. and Waterman, M. S. (1981) Ad. Appl Math., 2: 482–489, or Needleman, S. B. and Wunsch, C. D. (1970) J. Mol. Biol., 48: 443–453), to that of the present invention are included in the invention, as are proteins at least 70% or 80% and more preferably at least 90% identical to the protein of the present invention. This will generally be over a region of at least 20, preferably at least 30, contiguous amino acids.

Mutants, Variants and Homology—Nucleic Acids

Mutant polynucleotides will possess one or more mutations which are deletions, insertions, or substitutions of nucleotide residues. Mutants can be either naturally occurring (that is to say, isolated from a natural source) or synthetic (for example, by performing site-directed mutagensis on the DNA). It is thus apparent that polylnucleotides of the invention can be either naturally occurring or recombinant (that is to say prepared using recombinant DNA techniques).

An allelic variant will be a variant that is naturally occurring within an individual organism.

Nucleotide sequences are homologous if they are related by divergence from a common ancestor. Consequently, a species homologue of the polynucleotide will be the equivalent polynucleotide which occurs naturally in another species. Within any one species a homologue may exist as numerous allelic variants, and these will be considered homologues of the polynucleotide. Allelic variants and species homologues can be obtained by following standard techniques known to those skilled in the art. Preferred species homologues include those obtained from representatives of the same Phylum, more preferably the same Class and even more preferably the same Order.

A polynucleotide at least 70% identical, as determined by methods well known to those skilled in the art (for example, the method described by Smith, T. F. and Waterman, M. S. (1981) Ad. Appl Math., 2: 482–489, or Needleman, S. B. and Wunsch, C. D. (1970) J. Mol. Biol., 48: 443–453), to that of the present invention are included in the invention, as are proteins at least 80% or 90% and more preferably at least 95% identical to the polynucleotide of the present invention. This will generally be over a region of at least 60, preferably at least 90, contiguous nucleotide residues.

Antibody Production

The term "antibody" should be construed as covering any specific binding substance having a binding domain with the required specificity. Thus, the term covers antibody fragments, derivatives, functional equivalents and homologues of antibodies, including any polypeptide including an iimmunoglobulin binding domain, whether natural or synthetic. Chimaeric molecules including an immunoglobulin binding domain, or equivalent, fused to another polypeptide are therefore included.

Antibodies, either polyclonal or monoclonal, which are specific for a protein of the present invention can be produced by a person skilled in the art using standard techniques such as, but not limited to, those described by Harlow et al. Antibodies: A Laboratory Manual, Cold Springs Harbor Laboratory Press (1988), and D. Catty (editor), Antibodies: A Practical Approach, IRL Press (1988).

Various procedures known in the art may be used for the production of polycloiial antibodies to epitopes of a protein. For the production of polyclonal antibodies, a number of host animals are acceptable for the generation of antibodies by immunization with one or more injections of a polypeptide preparation, including but not limited to rabbits, mice, rats, etc. Various adjuvants may be used to increase the immunological response in the host animal, depending on the host species, including but not limited to Freund's (complete and incomplete), mineral gels such as aluminium hydroxide, surface active substances such as lysolecithin, pluronic polyols, polyanions, oil emulsions, keyhole lympet hemocyanins, dinitrophenol, and potentially useful human adjuvants such as BCG (*bacille* Calmette-Guerin) and *corynebacterium parvum*.

A monoclonal antibody to an epitope of a protein may be prepared by using any technique which provides for the production of antibody molecules by continuous cell lines in culture. These include but are not limited to the hybridoma technique originally described by Kohler and Milstein (1975, Nature 256, 493–497), and the more recent human B-cell hybridoma technique (Kesber et al. 1983, *Immunology Today* 4:72) and EBV-hybridoma technique (Cole et al. 1985, Monoclonal Antibodies and Cancer Therapy, Alan R. Liss, Inc. pp. 77–96). In addition, techniques developed for the production of "chimeric antibodies" by splicing the genes from an antibody molecule of appropriate antigen specificity together with genes from a human antibody molecule of appropriate biological activity may be used (Morrison et al. 1984, *Proc. Natl. Acad. Sci.*, 81:6851–6855; Neuberger et al. 1984 *Nature* 312:604–608; Takeda et al. 1985 *Nature* 31:452–454). Alternatively, techniques described for the production of single chain antibodies (U.S. Pat. No. 4,946,778) can be adapted to produce 4-specific single chain antibodies.

Recombinant human or humanized versions of monoclonal antibodies are a preferred embodiment for human therapeutic applications. Humanized antibodies may be prepared according to procedures in the literature (e.g. Jones et al. 1986, *Nature* 321:522–25; Reichman et al. 1988, *Nature* 332:323–27; Verhoeyen et al. 1988, *Science* 239:1534–36). The recently described "gene conversion mutagenesis" strategy for the production of humanized monoclonal antibody may also be employed in the production of humanized antibodies (Carter et al. 1992 *Proc. Natl. Acad. Sci. U.S.A.* 89:4285–89). Alternatively, techniques for generating the recombinant phage library of random combinations of heavy and light regions may be used to prepare recombinant antibodies (e.g. Huse et al. 1989 *Science* 246:1275–81).

Antibody fragments which contain the idiotype of the molecule such as Fu F(ab$^1$) and F(ab$^2$) may be generated by known techniques. For example, such fragments include but are not limited to: the F(ab) E2 fragment which can be produced by pepsin digestion of the intact antibody molecule; the Fab' fragments which can be generated by reducing the disulfide bridges of the F(ab')2 fragment, and the two Fab fragments which can be generated by treating the antibody molecule with papain and a reducing agent. Alternatively, Fab expression libraries may be constructed (Huse et al. 1989, *Science* 246:1275–1281) to allow rapid and easy cloning of a monoclonal Fab fragment with the desired specificity to a protein.

Adjuvants and Carriers

Pharmaceutically acceptable carriers or diluents include those used in compositions suitable for oral, rectal, nasal, topical (including buccal and sublingual), vaginal, parenteral (including subcutaneous, intramuscular, intravenous, intradermal, intrathecal and epidural) administration. They are non-toxic to recipients at the dosages and concentrations employed. Representative examples of pharmaceutically acceptable carriers or diluents include, but are not limited to water, isotonic solutions which are preferably buffered at a physiological pH (such as phosphate-buffered saline or Tris-buffered saline) and can also contain one or more of, mannitol, lactose, trehalose, dextrose, glycerol, ethanol or polypeptides (such as human serum albumin). The compositions may conveniently be presented in unit dosage form and may be prepared by any of the methods well known in the art of pharmacy.

As mentioned above the composition may include an adjuvant. As will be understood an "adjuvant" means a composition comprised of one or more substances that enhances the immunogenicity and efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol, vegetable oils such as peanut oil; *Corynebacterium*-derived adjuvants such as *Corynebacterium parvum*; *Propionibacterium*-derived adjuvants such as *Propionibacterium acne*; *Mycobacterium bovis* (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A almninium hydroxide; liposoines; ISCOM adjuvant; mycobacterial cell wall extract; synthetic glycopeptides such as murarmyl dipeptides or other derivatives; Avridine; Lipid A derivatives; dextran sulfate; DEAE-Dextran or with aluminium phosphate; carboxypolymethylene such as Carbopol' EMA; acrylic copolymer emulsions such as Neocryl A640 (e.g. U.S. Pat. No. 5,047,238); vaccinia or animal poxvirus proteins; sub-viral particle adjuvants such as cholera toxin, or mixtures thereof.

Gene/DNA Isolation

The DNA encoding a protein may be obtained from any cDNA library prepared from tissue believed to express the gene mRNA and to express it at a detectable level. DNA can also be obtained from a genomic library.

Libraries are screened with probes or analytical tools designed to identify the gene of interest or the protein encoded by it. For cDNA expression libraries, suitable probes include monoclonal or polyclonal antibodies that recognize and specifically bind the protein; oligonucleotides of about 20–80 bases in length that encode known or suspected portions of cDNA from the same or different species; and/or complementary or homologous cDNAs or fragments thereof that encode the same or a hybridizing gene. Appropriate probes for screening genomic DNA libraries include, but are not limited to, oligonucleotides; cDNAs or fragments thereof that encode the same or hybridizing DNA including expressed sequence tags and the like; and/or homologous genomic DNAs or fragments thereof. Screening the cDNA or genomic library with the selected probe may be conducted using standard procedures as described in chapters 10–12 of Sambrook et al.

An alternative means to isolate a gene encoding the protein of interest is to use polymerase chain reaction (PCR) methodology as described in section 14 of Sambrook et al. This method requires the use of oligonucleotide probes that will hybridize to the gene.

The oligonucleotide sequences selected as probes should be of sufficient length and sufficiently unambiguous that false positives are minimized. The actual nucleotide sequence(s) is usually based on conserved or highly homologous nucleotide sequences or regions of the gene. The oligonucleotides may be degenerate at one or more positions. The use of degenerate oligonucleotides may be of particular importance where a library is screened from a species in which preferential codon usage in that species is known. The oligonucleotide must be labelled such that it can be detected upon hybridization to DNA in the library being screened. The preferred method of labelling is to use ($\alpha$-$^{32}$P)— DATP with polynucleotide kinase, as is well known in the art, to radiolabel the oligonucleotide. However, other methods may be used to label the oligonucleotide, including, but not limited to, biotinylation or enzyme labelling.

DNA encompassing all the protein coding sequence is obtained by screening selected cDNA or genomic libraries, and if necessary, using conventional primer extension procedures as described in section 7.79 of Sambrook et al., to detect precursors and processing intermediates of mRNA that may not have been reverse-transcribed into cDNA.

Another alternative method for obtaining the gene of interest is to chemically synthesize it using one of the methods described in Fingels et al. (*Agnew Chem. Int. Ed.*

*Engl.* 28: 716–734, 1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

Substantially Purified

By "substantially purified" we mean a polypeptide that has been separated from lipids, nucleic acids, other polypeptides, and other contaminating molecules.

Hybridisation

The polynucleotide sequence of the present invention may hybridise to the respective sequence set out SEQ. ID. NOS. 2, 4, or 6 under high stringency. As used herein, stringent conditions are those that (i) employ low ionic strength and high temperature for washing after hybridization, for example, 0.1×SSC and 0.1% (w/v) SDS at 50° C.; (ii) employ during hybridization conditions such that the hybridization temperature is 25° C. lower than the duplex melting temperature of the hybridizing polynucleotides, for example 1.5× SSPE, 10% (w/v) polyethylene glycol 6000, 7% (w/v) SDS, 0.25 mg/ml fragmented herring sperm DNA at 65° C.; or (iii) for example, 0.5M sodium phosphate, pH 7.2, 5 mM EDTA, 7% (w/v) SDS and 0.5% (w/v) BLOTTO at 70° C.; or (iv) employ during hybridization a denaturing agent such as formamide, for example, 50% (v/v) formamide with 5×SSC, 50 mM sodium phosphate (pH 6.5) and 5× Denhardt's solution (32) at 42° C.; or (v) employ, for example, 50% (v/v) formamide, 5×SSC, 50 mM sodium phosphate (pH 6.8), 0.1% (w/v) sodium pyrophosphate, 5× Denhardt's solution, sonicated salmon sperm DNA (50 µg/ml) and 10% dextran sulphate at 42° C.

EXAMPLE 1

This example describes the cloning and characterisation of a protease from *Moraxella bovis*.

Bacteria and Construction of a Genomic Library

*Moraxella bovis* strain Dalton 2 d was a field isolate collected from a bovine eye and characterised by CSIRO Animal Health, Parkville, Australia (6). *Escherichia coli* strain DH5α has been previously described (7, 8).

All enzymes were purchased from Promega (Madison, Wis., USA) except where otherwise noted.

General cloning and DNA techniques were as described (9) unless otherwise noted.

A genomic library was constructed by carrying out partial Sau3A digests on genomic DNA extracted from *M. bovis* strain Dalton 2 d using a CTAB method which is outlined below. This DNA was size fractionated using a NaCl gradient (10) and ligated with the cosmid cloning vector pHC79 (11) which had been previously digested with BamHI. This DNA was packaged into lambda bacteriophage heads using the Packagene Lambda DNA packaging system (Promega, Madison, Wis., USA) and this was used to transduce the *E. coli* strain DH5α. The library was stored in 96 well trays (50% glycerol/luria broth/ampicillin (50 µg/ml)) at −70° C.

CTAB genomic DNA Extraction from *M. bovis*

A 5 ml brain heart infusion (BHI) (Oxoid Ltd., Basingstoke, Hampshire, U.K.) broth was inoculated with a colony of Dalton 2 d taken from a fresh overnight culture on horse blood agar and incubated with shaking at 37° C. for 6 hours. This culture was used to inoculate 50 ml of BHI broth which was grown with shaking at 37° C. overnight. 40 ml of the culture was transferred to an SS34 tube and the cells pelleted at 3000×g for 10 minutes. Following resuspension of the pellet in 9.5 ml of 25% sucrose in TE buffer (10 mM Tris, 1 mM EDTA (pH8)), 500 µl of 10% SDS, 50 µl of 20 mg/ml proteinase K and 20 µl of 10 mg/ml RnaseA were added and this mixture incubated in an orbital shaker for 1 hour at 37° C. To this mixture, 1.8 ml of 5M NaCl and 1.5 ml of a CTAB (N-Cetyl-N,N,N-trimethyl-ammonium bromide)/NaCl solution was added and incubation continued for 20 minutes at 65° C. The DNA was extracted using phenol/chloroform and precipitated with 0.6 volumes of isopropanol. The resulting DNA was washed in 70% ethanol, dried and resuspended in 2 ml of TE buffer.

Screening of Genomic Library for Enzyme Activity

The genomic library was cultured on skim milk agar to screen for the presence of a clone displaying protease activity (double strength Columbia agar base (Oxoid Ltd., Basingstoke, Hampshire, U.K.)/10% skim milk) for 24 hours at 37° C. followed by refrigeration at 4° C. for one to two days.

A single clone from the genomic library was detected as having activity against skim milk agar. DNA analysis confirmed that the clone contained a fragment of *M. bovis* Dalton 2 d genomic DNA approximately 40 kilobases in size. The construct was designated pJF1.

Nucleotide Sequence of the *M. bovis* Protease Clone pJF1

Plasmid and cosmid DNA for automated sequencing was extracted using the Wizard Plus SV Minipreps DNA Purification System (Promega, Madison, Wis., USA) and the Qiagen Plasmid Midi Kit (Qiagen Pty. Ltd., Clifton Hill, Vic, Australia), respectively.

The nucleotide sequence of the insert DNA was determined using the process of "primer walking" (12). This was achieved using synthetic oligonucleotides (Bresatec/Geneworks, Thebarton, SA, Australia) and the dye terminator cycle sequencing ready reaction (Perkin Elmer Corporation, Norwalk, Conn., USA). The resulting sequence was analysed on an Applied Biosystems 373A DNA sequencer.

Automated sequencing revealed an open reading frame of 3345 bp capable of encoding a protein of 1115 amino acids. The sequence is written in the 5' to 3' direction and is shown in FIG. 1 together with the corresponding amino acid sequence which is predicted to encode a protein with a molecular weight of 120 kDa. The amino acid sequence is shown in SEQ. ID. NO. 1 and the DNA sequence is shown in SEQ. ID. NO. 2.

The putative start codon for the mature protease protein was identified by the presence of a possible ribosome binding site upstream. This RBS was identified by its similarity to the consensus sequence for the *E. coli* RBS and that previously identified for the *M. bovis* pilin genes (AGGAG) (27).

Due to the secreted nature of the protease, it was assumed that it would contain in its N-terminal sequence a signal peptide which would be used in the secretion of the protein. This analysis was carried out using a prediction program (SignalP) available through the Expasy website (http://www.expasy.ch/tools/), which allows for the identification of prokaryotic signal peptides and predicts possible cleavage sites. This analysis only identified a signal peptide using the start codon indicated in the accompanying protein/DNA sequence.

Sequence Comparisons

Comparisons of the deduced amino acid sequence with those in the database were carried out using the BlastX and BlastP programs (13) which are available at http://www.ncbi.nlm.uih.gov.

At the amino acid level, the protease cloned from Dalton 2 d displayed the following similarity and identity to the proteins listed.

| Organism | Protein | Similarity | Identity |
|---|---|---|---|
| *Serratia marcescens* | ssp-h2 - serine protease autotransporter | 39% | 23% |
| *Serratia marcescens* | ssp-h1 - serine protease autotransporter | 37% | 22% |
| *Pseudomonas flourescens* | serine protease homologue | 34% | 20% |
| *Pseudomonas tolaasii* | serine protease | 35% | 21% |

More generally the 5' domain of the *M. bovis* protease displays homology to a family of subtilisins (serine proteases) while the 3' region resembles a number of outer membrane proteins.

The *M. bovis* sequence was found to contain a highly proline rich region which distinguished it from all other proteins to which it was closely related.

Protease Type Encoded by pJF1

In order to identify the type of protease activity encoded by pJF1, a range of specific protease inhibitors were examined for their effect on the expression of the *M. bovis* protease.

The method of Bourgeau et al., (1992) (14) was used to determine inhibitor activity with the following modifications. 100 μl of cell free supernatant from a fresh overnight broth culture was mixed with 650 μl of 100 mM Tris (pH 7.2) and a suitable volume of inhibitor PMSF (phenylmethylsulfonyl fluoride) 5 mM; EDTA 5 mM; leupeptin 100 μg/ml; pepstatin 50 μg/ml. Distilled water was used to make the volume up to 1 ml. The mixture was incubated at 37° C. for 30 minutes and 10 mg of azocoll (Calbiochem, Alexandria, NSW, Australia) was then added. The suspensions were incubated at 37° C. for 16 hours and the optical density read at 520 nm.

In this way it was confirmed that the activity attributable to the protease encoded by pJF1 was that of a serine protease since PMSF (a serine protease inhibitor) reduced the protease activity of both Dalton 2 d and pJF1 to zero.

Conservation of Protease in *M. bovis*

Southern hybridisation using an internal fragment of the protease coding region as a probe was carried out to investigate whether the protease was present in strains representing the known *M. bovis* pili serotypes.

Genomic DNA extracted from the representative strains of *M. bovis* (15) was digested with XbaI and EcoRI and separated using agarose gel electrophoresis. The DNA was transferred to a Hybond N+ filter (Amersham, Little Chalfont, Buckinghamshire, U.K.) using the method described (9). The probe used in the southern hybridisation was a PCR amplified fragment which was internal to the protease coding region. This fragment was labelled with $\alpha^{32}$P-dATP using the Megaprime labelling system (Amersham, Little Chalfont, Buckinghamshire, U.K.) according to the manufacturers instructions. High stringency conditions were used (hybridisation temperature 68° C.; 2 washes at room temperature in 2×SSC/0.1% SDS; 1 wash at 68° C. in 0.1×SSC/

0.1% SDS) and the resulting filters were exposed to autoradiographic film (Kodak, Rochester, N.Y., USA) for 5 to 24 hours before developing.

Results showed that the protease gene cloned in pJF1 is present in all strains of *M. bovis* examined.

EXAMPLE 2

This example describes the cloning and characterisation of a lipase from *Moraxella* bovis.

Bacteria and Construction of a Plasmid Library

*Moraxella bovis* strain Dalton 2 d was a field isolate collected from a bovine eye and characterised by CSIRO Animal Health, Parkville, Australia (6). *Escherichia coli* strain MC1061 has been previously described (16).

All enzymes were purchased from Promega (Madison, Wis., USA) except where otherwise noted. General cloning and DNA techniques were as described (9) unless otherwise noted.

A plasmid library was constructed in the cloning vector pBR322 (17). This was done by partially digesting genomic DNA extracted from Dalton 2 d (using the CTAB method described in Example 1) with Sau3A under conditions that maximised the amount of DNA in the range of 1 to 2 kb. This DNA was ligated with pBR322 which had been previously digested with BamHI. The ligated DNA was electroporated (2.5 kV, 200 Ω and 200 μF, for a theoretical time constant of 4.7) into electrocompetent *E. coli* MC1061 cells.

Screening of Plasmid Library for Lipase Expression

Following electroporation of the ligated DNA into MC1061 cells, recombinant clones displaying lipase activity were detected by culturing the library for 24 hours at 37° C. on media containing Tween 80 [10 ml Tween 80 (Sigma, St Louis, Mo., USA), 5 g NaCl, 3 g agar No. 1 (Oxoid Ltd., Basingstoke, Hampshire, U.K.), log peptone, 0.1 g $CaCl_2.H_2O$/liter].

Twenty eight out of 24,000 clones screened were found to be displaying lipase activity. DNA analysis confirmed that all of these clones contained one 5.4 kb fragment of DNA in common. One clone was chosen to continue work with and this was designated pMB1.

In some experiments (below), a photometric assay of extracellular lipase activity was performed with p-nitrophenylpalmitate as the substrate (18, 19). Strains of *E. coli* and/or *M. bovis* were grown at 37° C. for the required time points. Cell free culture supernatant (100 μl) was mixed with 2.4 ml of enzyme buffer (19) to assay secreted lipase activity. After 30 minutes incubation at 37° C., the optical density at 410 nm was determined. One enzyme unit was defined as the amount of enzyme that releases 1 nmol of p-nitrophenyl from p-nitrophenylpalmitate $ml^{-1}$ $min^{-1}$. Under the conditions described by Stuer et al., (18), an optical density at 410 nm of 0.041 is equivalent to 1 enzyme unit.

Nucleotide Sequence of the *M. bovis* lipase clone pMB1

Plasmid pMB1 was subjected to automated DNA sequencing using the methodology described in Example 1.

This analysis revealed an open reading frame of 1851 bp capable of encoding 617 amino acids. The sequence is written in the 5' to 3' direction and is shown in FIG. 2 together with the corresponding amino acid sequence that is predicted to encode a protein with a molecular weight of 65.8 kDa. The amino acid sequence is shown in SEQ. ID. NO. 3 and the DNA sequence is shown in SEQ. ID. NO. 4.

The techniques set out above in respect of the protease were used to identify the potential start codon for the lipase protein.

Sequence Comparisons

Sequence comparisons were made using the methodology described in Example 1.

At the amino acid level, the lipase cloned from *M. bovis* Dalton 2 d was shown to display the following similarity and identity to the proteins listed.

| Organism | Protein | Similarity | Identity |
|---|---|---|---|
| *Xenorhabdus luminescens* | triacyiglycerol lipase | 36% | 24% |
| *Pseudumonas putida* | hypothetical protein | 36% | 24% |
| *Salmonella typhimurium* | outer membrane esterase | 35% | 23% |
| *Pseudomonas aeruginosa* | lipase/esterase | 36% | 23% |

The *M. bovis* lipase was identified as being a possible new member of the GDSL family (20) of lipolytic enzymes. N-terminal sequencing carried out on the lipase mature protein The required strains of *E. coli* were cultured overnight with shaking at 37° C. in 500 mls of luria broth. The cells were pelleted at 5,000 rpm for 15 mins and the supernatant filtered through a 0.45 μm filter. Solid ammonium sulfate was added to the supernatant to 60% saturation (180 g/500 ml), and dissolved at 4° C. with stirring for 30 minutes. This mixture was left at 4° C. overnight and the precipitated proteins pelleted at 7,000 rpm for 30 mins. The proteins were resuspended in 3 ml of double distilled water and the solubilised proteins dialysed against double distilled water overnight to remove any salt. The resulting mixture was filtered through a 0.45 μm filter and stored at −20° C.

Following separation of the proteins by SDS-PAGE, the proteins were transferred to PVDF membrane and excised. The protein was subjected to automated (Edman degradation) sequence analysis (28) with vapour phase delivery of critical reagents (29) in an automated sequenator (model 470A; Applied Biosystems) (Applied Biosystems Division, Foster City, Calif., USA) in conjunction with a PTH amino acid separation system (model 120A PTH analyzer; Applied Biosystems).

Using this technique 17 amino acids with two gaps were identified

KEFSQVIIFGDSLXDXG (SEQ ID NO:7)

which corresponds exactly with amino acids 26 through to 42 shown on the accompanying sequence. This result also indicated that the protein most likely includes an amino terminal signal peptide which is involved in the secretion of the protein. This amino terminal corresponds to amino acids 1 through to 25 in the accompanying sequence.

Raising Antibodies to the Lipase in Rabbits

Antibody to the recombinant lipase was raised in rabbits by injecting ammonium sulfate precipitated supernatant from *E. coli* MC1061/pMB4. Prior to vaccination, the lipase preparation was inactivated by heating to 90° C. for 90 min. 30 μg of this protein was injected at 2 weekly intervals for 4 weeks. The primary inoculum was emulsified with Freunds complete adjuvant and subsequent vaccinations with Freunds incomplete adjuvant.

Heat Stability of *M. bovis* Lipase The recombinant lipase cloned from *M. bovis* Dalton 2 d was found to be very heat stable since it required heating at 90° C. for 105 minutes for the activity to be reduced by 97%. FIG. 3 illustrates this phenomenon with enzyme activity expressed as "lipase enzyme units" as determined in the extracellular lipase assay.

Relative Expression Levels of Native Versus Recombinant Lipase

An experiment was performed to plot growth rate with lipase production and to compare production of the recombinant lipase from MC1061/pMB1 with that of the native form of the lipase from *M. bovis* Dalton 2 d. FIG. 4 illustrates that the two strains grow at approximately the same rate but they do not reach the same cell density, with Dalton 2 d substantially lower after 9 hours than MC1061/pMB1. Lipase expression levels were greatest from the pMB1 construct in *E. coli* compared to native lipase expression from *M. bovis* Dalton 2 d.

This result was further substantiated when proteins from cell-free supernatants of either the *E. coli* clone or *M. bovis* Dalton 2 d were ammonium sulfate precipitated and analysed by SDS-PAGE and western blot using antisera to the recombinant heat-deactivated lipase.

Ammonium sulfate precipitated supernatants were prepared from overnight cultures of *E. coli* or *M. bovis* that had been shaken at 37° C. in either 500 mls of Luria broth or brain heart infusion broth, respectively. Cells were pelleted at 5000×g for 15 minutes and the supernatant filtered through a 0.45 μm filter. Solid ammonium sulfate was added to the supernatant to 60% saturation (180 g/500 ml) and dissolved at 4° C. with stirring for 30 minutes. This mixture was left at 4° C. overnight and the precipitated protein pelleted at 7000×g for 30 minutes. Proteins were resuspended in 3 ml of double distilled water and the solubilised proteins dialysed against double distilled water overnight to remove any salt. The resulting mixture was filtered through a 0.45 μm filter and stored at −20° C.

Protein samples (100 μl) were prepared for SDS-PAGE by resuspension in 100 μl of 2× sample buffer (5 ml 0.5M Tris (pH6.8), 8 ml 10% SDS, 4 ml glycerol, 0.8 ml β-mercaptoethanol, 1 ml double distilled $H_2O$, bromophenol blue) and heating to 100° C. for 5 minutes. The proteins were separated on a 12.5% polyacrylamide gel using the buffer system of Laemlli (21).

Western blots were carried out according to the method of Towbin et al., (22) and following separation of proteins by SDS-PAGE and transfer to nitrocellulose using the Bio-Rad minicell (Bio-Rad, Hercules, Calif., USA) transfer system. Filters were immunoblotted with the recombinant lipase antiseruin (at a concentration of 1/100) which had been adsorbed against MC1061 cells. The antiserum was raised against ammonium sulfate precipitated recombinant lipase which had been heat deactivated (1 hour 45 minutes at 90° C.) and used to inoculate rabbits (three doses of 50%1 g each) at 4 week intervals. Blood samples were collected from the marginal ear vein prior to immunisation and at each vaccination time point.

The results showed a prominent band present in the recombinant lipase positive construct MC1061/pMB1 that is detectable in relatively minor amounts in *M. bovis* Dalton 2 d preparation. The protein detected with the antisera was approximately the same size as that of the predicted molecular weight for the *M. bovis* lipase (65.8 kDa).

Lipase Type Encoded by pMB1

Thin layer chromatography (TLC) was used to determine whether the lipase of *M. bovis* Dalton 2 d displayed phospholipase activity. Characterisation of phospholipase type essentially followed a previously described method (23) except that the results of separation on Silica Gel 60 plates were visualised by developing with a 10% ethanolic solution of molybdophosphoric acid at 100° C. All reagents used were purchased from Sigma (Sigma, St Louis, Mo., USA).

TLC determined that the *M. bovis* lipase displayed the same enzyme specificity as that of a commercially-available phospholipase B when lysophosphatidylcholine and phosphatidylcholine were used as substrates (data not shown).

Conservation of Lipase Among *M. bovis*

A southern blot using an internal fragment of the Dalton 2 d lipase coding region was used to investigate whether the lipase gene was present in strains of *M. bovis* representing the known pilus serotypes.

Genomic DNA extracted from the strains of *M. bovis* representing each of the known pilus serotypes (15) was digested with HindIII and separated using agarose gel electrophoresis. The DNA was transferred to a Hybond N+ filter (Amersham, Little Chalfont, Buckinghamshire, U.K.) using a previously described method (9). The probe used in the southern hybridisation was a HindIII fragment that contained sequence internal to the lipase coding region. This fragment was labelled with $\alpha^{32}$P-dATP using the Megaprime labelling system (Amersham, Little Chalfont, Buckinghamshire, U.K.) according to the manufacturers instructions. High stringency conditions were used (hybridisation temperature 68° C.; 2 washes at room temperature in 2×SSC/0.1% SDS; 1 wash at 68° C. in 0.1×SSC/0.1% SDS) and the resulting filters were exposed to autoradiographic film (Kodak, Rochester, N.Y., USA) for 5 to 24 hours before developing.

Results showed that the lipase gene is present in all strains of *M. bovis* examined.

To confirm whether or not the lipase gene was expressed in each of the serotype representative strains, antisera raised against recombinant heat deactivated lipase was used in a western blot analysis of whole cell preparations. Results showed that the lipase was indeed being expressed by all of these *M. bovis* strains.

EXAMPLE 3

Bacteria and Construction of a Haemolysin Clone

*Moraxella bovis* strain Dalton 2 d was a field isolate collected from a bovine eye and characterised by CSIRO Animal Health, Parkville, Australia (6).

All of the *M. bovis* strains representative of the known pilus serotypes express a haemolytic activity that is detected on horse blood agar.

*Escherichia coli* strain degP4::Tn5 has a leaky outer membrane and is defective in proteolysis and has been previously described (24). All enzymes were purchased from Promega (Madison, Wis., USA) except where otherwise noted.

General cloning and DNA techniques were as described (9) unless otherwise noted.

A phoA fusion technique that allows for the identification of exported proteins (25) was utilised with some modifications. Genomic DNA from *M. bovis* Dalton 2 d (prepared using the CTAB method described in Example 1) was partially digested with Sau3A. Restricted DNA was ligated with a series of vectors that allow fusions with an alkaline phosphatase gene in three different reading frames. The ligated DNA was electroporated into *E. coli* degP4::Tn15 and the resulting clones screened on Luria agar containing ampicillin (50 μg/ml) and X—P (200 μg/ml) (5-bromo-3-chloro-indolyl phosphate). Selection of clones relies on the observation that if the fragment is cloned in frame and contains an export sequence the resulting colony will be blue in colour. The leaky *E. coli* strain allows the outer membrane-bound proteins and secreted proteins (both fused with phoA) to be distinguished from non-secreted fusion proteins.

Sequencing of the *M. bovis* Haemolysin Determinant

Clones selected for the presence of a secreted or outer membrane protein gene sequence were subjected to automated DNA sequencing using the methods described in Example 1. One of these clones, pMbh1, was found to contain 200 bp of DNA which displayed high homology to the A subunit of other RTX toxins. Inverse PCR and degenerate oligonucleotides were utilised to obtain the sequence of the entire A subunit. The open reading frame of 2784 bp was capable of encoding 928 amino acids. The sequence is written in the 5' to 3' direction and is shown in FIG. 5 together with the corresponding amino acid sequence that is predicted to encode a protein with a molecular weight of 98.8 kDa. The amino acid sequence is shown in SEQ. ID. NO. 5 and the DNA sequence is shown in SEQ. ID. NO. 6.

The putative start codon was identified using the RBS technique outlined above. A signal peptide analysis was not carried out as the A subunit is not secreted on its own. However as the protein sequence of these proteins (RTX) is quite highly conserved, on amino acid homologies alone this start codon was the one of choice.

Sequence Homology

At the amino acid level the *M. bovis* Dalton 2 d haemolysin gene product shows striking similarity to the A subunit of the of several RTX and other haemolysins as shown in the following table.

| Organism | Protein | Similarity | Identity |
|---|---|---|---|
| *Pasteurella haemolytica* | LktA protein (leukotoxin) | 68% | 50% |
| *Actinobacillus pleuropneumoniae* | RTX toxin determinant | 68% | 48% |
| *Escherichia coli* | Haeinolysin - plasmid | 58% | 43% |
| *E. coli* | Haemolysin - chromosomal | 58% | 43% |

Functional Complementation by the *M. bovis* Haemolysin

A construct which expressed the chromosomal-borne haemolysin of *E. coli* was obtained (pLG900; generated by combining the two plasmids pLG575 (26) and pLG816 (hlyC and hlyA cloned into pBluescriptSK). pLG900 comprises the four genes of the RTX operon, hlyC, hlyA, hlyB, hlyD, cloned into pBluescriptSK and is capable of conferring a haemolytic phenotype on *E. coli* cells that were previously non-haemolytic. The A subunit (hlyA) of this construct was mutated such that it was no longer able to be expressed but the other genes involved in the operon (hlyB, hlyC and hlyD) remained intact. The *E. coli* strain containing this construct (pLG900/hlyA negative) was no longer haemolytic. However, the haemolytic phenotype was restored by providing in trans the cloned haemolysin subunit gene from *M. bovis* Dalton 2 d. Thus it was confirmed that the cloned *M. bovis* haemolysin gene encoded a structural subunit that was most probably a member of the RTX family of haemolytic enzymes.

Further sequence analysis has established that, like other members of the family, the *M. bovis* RTX A subunit gene is flanked by DNA sequences capable of encoding the RTX B,C and D proteins.

Conservation of the RTX A Subunit among *M. bovis*

To determine whether the gene for the RTX A subunit was present in *M. bovis* strains representing the known pilus serotypes, a southern hybridisation analysis was performed using the coding region of the RTX A subunit as a probe.

Genomic DNA extracted from the seven serotype strains of *M. bovis* (15) was digested with EcoRV and separated using agarose gel electrophoresis. The DNA was transferred to a Hybond N+ filter (Amersham, Little Chalfont, Buckinghamshire, U.K.) using a previously described method (9). The probe used was a PCR amplified product that contained all of the coding region from the A subunit of the RTX haemolysin of *M. bovis*. This fragment was labelled with $\alpha^{32}$P-dATP using the Megaprime labelling system (Amersham, Little Chalfont, Buckinghamshire, U.K.) according to the manufacturers instructions. High stringency conditions were used (hybridisation temperature 68° C.; 2 washes at room temperature in 2×SSC/ 0.1% SDS; 1 wash at 68° C. in 0.1×SSC/0.1% SDS) and the resulting filters were exposed to autoradiographic film (Kodak, Rochester, N.Y., USA) for 5 to 24 hours before developing.

Results showed that the gene encoding the RTX A haemolysin subunit was conserved in all seven representative strains of *M. bovis* examined. Interestingly, each of these strains is known to display the haemolytic phenotype on horse blood agar. In contrast, the non-haemolytic *M. bovis* strain Gordon 26L3 did not hybridise to the RTX A gene probe possibly suggesting that *M. bovis* contains only a single structural gene responsible for the haemolytic phenotype detected on horse blood agar.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Moore L. J., and A. W. D. Lepper. (1991). Vet Microbiol. 29:75–83.
2. Lehr, C. H., G. Jayappa and R. A. Goodnow. (1985). Cornell Vet. 75:484–492.
3. Pugh, G. W., D. E. Hughes and G. D. Booth. (1977). Am J Vet Res. 38:1519–1522.
4. Frank, S. K., and J. D. Gerber. (1981). J Clin Microbiol. 13(2):269–271.
5. Billson, F. M., J. L. Hodgson, A. W. Lepper, W. P. Michalski, C. L. Schwartzkoff, P. R. Lehrbach, and J. M. Tenlent. (1994). FEMS Microbiol Lett. 124(1):69–73.
6. Elleman, T. C., P. A. Hoyne, and A. W. D. Lepper. (1990). Infect Immun. 58(6):1678–1684.
7. Woodcock, D. M., P. J. Crowther, J. Doherty, S. Jefferson, E. DeCruz, M. Noyer-Weidner, S. S. Smith, M. Z. Michael, and M. W. Graham. (1989). Nucleic Acids Res. 17(9):3469–3478.
8. Raleigh, E. A., K. Lech, and R. Brent. (1989). In Current Protocols in Molecular Biology eds. Ausubel, F. M. et al., Publishing Associates and Wiley Interscience; New York. Unit 1.4.

9. Sambrook, J., E. F. Fritsch, and T. Maniatis. (1989). Molecular Cloning: A Laboratory Manual, 2nd edition. Cold Spring Harbour Laboratory Press, Cold Spring Harbour, N.Y.
10. Dillela, A. G., and S. L. C. Woo. (1985). Focus. 7(2):1–5.
11. Hohn, B., and J. Collins. (1980). Gene. 11(3–4):291–298.
12. Narberhaus. F., K. Giebeler, and H. Bahl. (1992). J. Bacteriol. 174(10):3290–3299.
13. Altschul, S. F., T. L. Madden, A. A. Schaffer, Z. Jinghui, Z. Zhang, W. Miller, and D. J. Lipman. (1997). Nucleic Acids Res. 25:3389–3402.
14. Bourgeau, G., H. Lapointe, P. Peloquin, and D. Mayrand. (1992). Infection and Immunity. 60(8):3186–3192.
15. Ausubel, F. M. R. Brent, R. E. Kingston, D. D. Moore, J. G. Seidman, J. A. Smith, and K. Struhl. (1994). Current Protocols in Molecular Biology. Green Publishing Associates, Inc. and John Wiley and Sons Inc. New York.
16. Wertman, K. F., A. R. Wyman, and D. Botstein. (1986). Gene. 49(2):253–262.
17. Bolivar F., R. L. Rodriguez, P. J. Greene, M. C. Betlach, H. L. Heynecker, and H. W. Boyer. (1977). Gene. 2(2): 95–113.
18. Stuer, W., K. E. Jaeger, and U. K. Winkler. (1986). J. Bacteriol. 168:1070–1074.
19. Winkler, U. K., and M. Stuckman. (1979). J. Bacteriol. 138:663–670.
20. Upton, C., and J. T. Buckley. (1995). Trends Biochem Sci. 20(5):178–9.
21. Laemmli, U. K. (1970). Nature. 227(259):680–685.
22. Towbin, H., T. Staehlin, and J. Gordon. (1979). Proc Natl Acad Sci USA. 76(9):4350–4354.
23. Fifis, T., C. Costopoulos, and J. A. Vaughn. (1996). Vet Microbiol. 49:219–233.
24. Strauch, K. L., and J. Beckwith. (1988). Proc Natl Acad Sci USA. 85(5):1576–1580.
25. Gilaldi, M., C. I. Champion, D. A. Haake, D. R. Blanco, J. F. Miller, J. N. Miller, and M. A. Lovett. (1993). J. Bacteriol. 175:4129–4136.
26. Mackman, N., J-M. Nicaud, L. Gray, and I. B. Holland. (1985). Mol Genet. 201:282–288.
27. Atwell, J. L., J. M. Tennent, A. W. Lepper and T. C. Elleman. (1994). J Bacteriol 176(16):4875–82.
28. Edman, P., and C. Begg. (1967). Eur. J. Biochem. 1:80–91.
29. Hewick, R. M., M. W. Hunkapillar, L. E. Hood, and W. J. Dreyer. 1981. J Biol. Chem. 256: 7990–7997

We claim:

1. An isolated polypeptide comprising the amino acid sequence as set out in SEQ ID NO: 5.

2. The polypeptide, as claimed in claim 1, having haemolysin activity.

3. A composition for use in raising an immune response in an animal, the composition comprising a substantially purified polypeptide having the amino acid sequence as set out in SEQ ID NO: 5 and optionally a carrier and/or adjuvant.

* * * * *